US008974782B2

(12) United States Patent
Abila et al.

(10) Patent No.: US 8,974,782 B2
(45) Date of Patent: Mar. 10, 2015

(54) TREATMENT OF STROKE COMPRISING ANTI-MAG ANTIBODIES

(75) Inventors: Bams Abila, Stevenage (GB); Lori Ann Enney, Durham, NC (US); Seth Paul Finklestein, Durham, NC (US); Volker Germaschewski, Stevenage (GB); Robert Ian Grundy, Stevenage (GB); Elaine Alison Irving, Stevenage (GB); Monica Simeoni, Middlesex (GB)

(73) Assignee: Glaxo Group Limited (GB)

( * ) Notice: Subject to any disclaimer, the term of this patent is extended or adjusted under 35 U.S.C. 154(b) by 0 days.

(21) Appl. No.: 13/367,754

(22) Filed: Feb. 7, 2012

(65) Prior Publication Data
US 2012/0207749 A1 Aug. 16, 2012

Related U.S. Application Data

(60) Provisional application No. 61/440,119, filed on Feb. 7, 2011, provisional application No. 61/448,365, filed on Mar. 2, 2011.

(51) Int. Cl.
*A61K 39/395* (2006.01)
*A61P 25/00* (2006.01)
*A61P 7/04* (2006.01)
*A61P 9/10* (2006.01)
*C07K 16/28* (2006.01)
*A61K 39/00* (2006.01)

(52) U.S. Cl.
CPC ....... *C07K 16/2803* (2013.01); *A61K 2039/505* (2013.01); *A61K 2039/54* (2013.01); *A61K 2039/545* (2013.01); *C07K 2317/90* (2013.01); *Y10S 530/866* (2013.01)
USPC ....... 424/130.1; 530/866; 514/17.7; 514/18.2

(58) Field of Classification Search
None
See application file for complete search history.

(56) References Cited

U.S. PATENT DOCUMENTS 4,873,316 A  10/1989  Meade et al.

FOREIGN PATENT DOCUMENTS

| WO | WO95/22344 | 8/1995 |
| WO | WO96/16990 | 6/1996 |
| WO | WO97/01352 | 1/1997 |
| WO | WO97/07810 | 2/1997 |
| WO | WO99/58679 | 11/1999 |
| WO | WO02/062383 | 8/2002 |
| WO | WO2004/024953 A2 | 2/2004 |
| WO | WO 2004014953 | * 2/2004 |
| WO | WO2004/083363 A2 | 9/2004 |
| WO | WO 2007033230 | * 3/2007 |

OTHER PUBLICATIONS

ClinicalTrials.gov identifier: NCT0833989, published on Feb. 1, 2009 [online] Retrieved from: <http://clinicaltrials.gov/archive/NCT00833989/2009_02_01> Retrieved on May 15, 2013.*
Kabat, et al., "Sequences of Proteins of Immunological Interest", 4th Ed., U.S. Department of Health and Human Services, National Institutes of Health (1987).
Lassman, et al., Glia, 19, 104-110 (1997).
Lee, et al., J Neuroscience, 2004, 24(27):6209-6217.
Li, et al., Neurobiology of Disease, 2006, 23:362-373.
Mears, et al., Journal of the Peripheral Nervous System. 2003, 8:91-99.
Miller, et al., "Genetic Engineering", 8:277-298, Plenum Press (1986).
Modo, M., et al., "Neurological sequelae and long-term behavioural assessment of rats with transient middle cerebral artery occulsion", Journal of Neuroscience Methods, 104 (2000), 99-109.
Montoya, C.P., et al., "The "staircase test" measure of independent forelimb reaching and grasping abilities in rats", Journal of Neuroscience Methods, 36 (1991), 219-228.
Nudo, R.J. and Milliken G.W., "Reorganization of movement representations in primary motor cortex following focal ischemic infarcts in adult squirrel monkeys", Journal of Neurophysiology, 1996, 75:5, 2144-2149.
Nudo, R.J., et al., "Neurophysiological Correlates of Hand Preference in Primary Motor Cortex of Adult Squirrel Monkeys", The Journal of Neuroscience, Aug. 1992, f(8): 2918-2947.
Plautz, EJ, et al., "Effects of Repetitive Motor Training on Movement Representations in Adult Squirrel Monkeys: Role of Use versus Learning", Neurobiology of Learning and Memory, 74, 27-55 (2000).
Poltorak, et al., (1987), *Journal of Cell Biology*, 105, 1893-1899.
Sandoval, Karin E., Witt, Ken A., "Blood-brain barrier tight junction permeability and ischemic stroke", Neurobiology of Disease, 32, (2008), 200-219.
Schallert, Timothy, et al., "CNS plasticity and assessment of forelimb sensorimotor outcome in unilateral rat models of stroke, cortical ablation, parkinsonism and spinal cord injury", Neuropharmacology, 39 (2000), 777-787.
Tang et al., (1997), *Mol. Cell. Neurosci.*, 9, 333-346.
Torigoe, et al al., Experimental Neurology. 1998, 150:254-262.
Umemori, et al., 1994, Nature, 367, 572-576.
Virley, David, at al., "A Temporal MRI Assessment of Neuropathology After Transient Middle Cerebral Artery Occlusion in the Rat: Correlations With Behavior", *Journal of Cerebral Blood Flow & Metabolism*, (2000) 20, 563-582).
WM Jenkins and MM Merzenich (1987), "Reorganization of neocortical representations after brain injury: a neurophysiological model of the bases of recovery from stroke", Progress in Brain Research, 71:249-66.
Chothia, et al., 1989, "Conformations of immunoglobulin hypervariable regions", Nature, 342, p. 877-883.
DeBellard, et al., (1996), *Mol. Cell. Neurosci.*, 7, 89-101.
Duncan, A.R. Nature, v332, p. 738-740, 1988.

(Continued)

*Primary Examiner* — Daniel E Kolker
*Assistant Examiner* — Stacey N MacFarlane
(74) *Attorney, Agent, or Firm* — Jason C. Fedon; William T. Han

(57) ABSTRACT

The present invention relates to a dosing regimen for use in the treatment of stroke. More particularly, the invention relates to the administration of two doses of anti-MAG antibodies for the treatment of ischemic and/or haemorrhagic stroke.

14 Claims, 15 Drawing Sheets

(56) References Cited

OTHER PUBLICATIONS

Frost, S.B., et al., (2003) "Reorganization of remote cortical regions after ischemic brain injury: a potential substrate for stroke recovery", Journal of Neurophysiology, 89:3205-3214.

Gould, et al., (1986) "The relationship of corpus callosum connections to electrical stimulation maps of motor, supplementary motor, and the frontal eye fields in owl monkeys", Journal of Comparative Neurology, 247:297-325.

GrandPre, et al., Nature, 2002, 417(6888):547-551.

Grundy, et al., J. Cerebral Blood Flow & Metabolism 2005, 25, S233.

Guadagno, et al., Brain, 2008, 131:2666-2678.

Irving EA, et al., "Assessment of white matter injury following prolonged focal cerebral ischaemia in the rat", Acta Neuropathol, (2001) 102, 627-635.

Irving, et al., "Increased cortical expression of the orexin-1 receptor following permanent middle cerebral artery occlusion in the rat", Neurosci Lett., May 2002, 10, 324(1):53-6.

Irving, et al., J. Cerebral Blood Flow & Metabolism 2005, 25, 98-107.

* cited by examiner 2 way repeated measures ANOVA & Bonferroni post-hoc test comparing either hemisphere to their pre-lesion baseline: *** $p<0.001$, * $p<0.05$ for the lesioned hemisphere, § § $p<0.01$ for the contralateral hemisphere 2 way repeated measures ANOVA & Bonferroni post-hoc test comparing either hemisphere to their pre-lesion baseline: * $p<0.001$,  $p<0.01$, * $p<0.05$ for the lesioned hemisphere;

§ § § $p<0.001$, § § $p<0.01$ for the contralateral hemisphere

Figure 19

SCRIPT 1

$PROB MAG FTIH fitting PK dataset December 2010

$INPUT ID SUBJ TIME DV DAY WK DGRP coho MDV AMT RATE ADDL II EVID $DATA datafile13Dec10.dat IGNORE=@

$SUB ADVAN3 TRANS4

$PK

D1=1

CL = THETA(1)*EXP(ETA(1)) ; ml/kg/h

V2= THETA(2)*EXP(ETA(2)) ; ml/kg

V1=THETA(3)*EXP(ETA(3)) ; ml/kg

VSS = V1+V2 ; ml/kg

DVZ = THETA(4)*EXP(ETA(4)) ; ml/kg

VZ = V1 + V2 + DVZ ; ml/kg

Q = CL*(V2/DVZ)*(V2+DVZ)/VZ ; ml/kg/h

F1=1

S1 = V1 ; ml/kg

AUC = F1*DGRP/CL; mg.hr/ml

CMAX = F1*DGRP*1000/V1; ug/ml

K12=Q/V1 ; 1/hr

K21=Q/V2 ; 1/hr

K=CL/V1 ; 1/hr

ALPHA=1/2*(K12+K21+K)+1/2*SQRT((K12+K21+K)**2-4*K*K21) ; 1/hr

BETA=1/2*(K12+K21+K)-1/2*SQRT((K12+K21+K)**2-4*K*K21) ; 1/hr

AOB= (ALPHA-K21)/(K21-BETA)

HL=LOG(2)/BETA/24 ; days $ERROR

IPRED   = F

IRES    = DV-IPRED

W= F

QQ=1

IF (IPRED.EQ.0) QQ=0

IWRES    =QQ*IRES/(1-QQ+W)

Y     = F*(1+EPS(1))

$THETA
(0.005 0.0643 1) ; CL
(0.1 17.0 50); V2
(10 28.3 100) ;V1
(0.01 1.71 100) ;DVZ
$OMEGA 0.0256  0.0347  0.0203  0.0894 FIXED ; from the FTIH
$SIGMA 0.00692
$EST MAXEVAL=9999 NOABORT METHOD=1 INTER
$COV
$TABLE ID SUBJ DGRP TIME MDV DAY IPRED IRES IWRES CMAX AUC CL V1 Q V2 VSS VZ HL FILE=sdtab1 NOPRINT

TREATMENT OF STROKE COMPRISING ANTI-MAG ANTIBODIES

FIELD OF THE INVENTION

The present invention relates to a particular dosing regimen for use in the treatment of neurological diseases, in particular stroke. More particularly, the invention relates to the administration of two doses of anti-myelin-associated glycoprotein (anti-MAG) antibodies for the treatment of ischemic stroke and/or haemorrhagic stroke.

BACKGROUND OF THE INVENTION

Myelin-associated glycoprotein (MAG) is a cell surface transmembrane molecule expressed on the surface of myelin consisting of five extracellular immunoglobulin domains, a single transmembrane domain and an intracellular domain. MAG expression is restricted to myelinating glial cells: oligodendrocytes in the central nervous system and Schwann cells in the peripheral nervous system. MAG interacts with neuronal receptor(s) which initiate bi-directional signalling between neurons and glia. The effect of MAG binding to neuronal receptors is known to result in inhibition of neurite outgrowth in vitro. Based on this in vitro data, antagonists of MAG have been postulated as useful for the promotion of axonal sprouting following injury (WO95/22344, WO97/01352 and WO97/07810), although these claims are not supported by in vivo data. WO02/062383 discloses that an anti-MAG antibody, when administered directly into the brain or intravenously following focal cerebral ischaemia in the rat (a model of stroke) provides neuroprotection and enhances functional recovery.

Evidence in the literature suggests that MAG also mediates signalling into glial cells, but the functional significance of this has not been understood. It has been reported that engagement of MAG expressed at the surface of a CHO cell using an antibody leads to the activation of fyn kinase (Umemori et al., 1994, Nature, 367, 572-576). Furthermore, MAG knockout animals exhibit defects in myelin which resemble aspects of the defective changes observed in the brains of multiple sclerosis and encephalomyelitis patients (Lassman et al., Glia, 19, 104-110).

In animals, neutralisation of MAG following neuronal injury has been shown to promote regeneration in peripheral and central nerves (Torigoe et al., Experimental Neurology. 1998, 150:254-262; Mears et al., Journal of the Peripheral Nervous System. 2003, 8:91-99). Data from pre-clinical studies demonstrate that promotion of regeneration following neuronal injuries can enhance recovery (Lee et al., J Neuroscience, 2004, 24(27):6209-6217; GrandPre et al., Nature, 2002, 417(6888):547-551). In stroke patients, there is continued loss of neurons in the penumbra as shown by $^{11}$C-Flumazenil PET (Guadagno et al., Brain, 2008, 131:2666-2678). In rats with stroke induced by MCAO, MAG expression (mRNA and protein) is significantly upregulated in the peri-infarct area for several weeks after MCAO (Li et al., Neurobiology of Disease, 2006, 23:362-373). It is hypothesized that this over-expression of MAG may, at least in part, account for the continued loss of neurons and failure of neuro-regeneration after stroke.

PCT application PCT/EP2004/001016 (published as WO2004/083363 A2) discloses a method of promoting oligodendrocyte survival in a human suffering or at risk of developing stroke or another neurological disease which comprises administering to said human a therapeutically effective amount of an anti-MAG antibody or a functional fragment thereof.

PCT application PCT/EP2003/008749 (published as WO2004/014953 A2) discloses altered antibodies to myelin associated glycoprotein, pharmaceutical compositions containing them and to the use of such antibodies in the treatment and/or prophylaxis of neurological diseases/disorders, such as stroke.

PCT application PCT/GB2002/000551 (published as WO2002/062383 A2) discloses a method of treatment of neurological diseases and antibodies for use in such method.

Irving et al., J. Cerebral Blood Flow & Metabolism, "Identification of neuroprotective properties of anti-MAG antibody: a novel approach for the treatment of stroke?", 2005, 24, 98-107 relates to a commercially available anti-MAG antibody administered either intracerebrally at 1, 24 or 72 hours post-MCAO in the rat, or intravenously at 1 and 24 hours post-MCAO.

Grundy et al., J. Cerebral Blood Flow & Metabolism, "Functional recovery and increased PSA-NCAM expression following delayed administration of an anti-MAG antibody post stroke in the rat, 2005, 25, S233 related to two doses of a commercially available anti-MAG antibody administered intracerebroventirularly 24 hours apart, starting at 1, 6 or 24 hours following tMCAO.

Dr Steve Cramer presented a poster, entitled "A single-blind Study of the Safety, Pharmacokinetics, and Pharmacodynamics of Escalating Repeat Doses of GSK249320 in Patients with Stroke" at the 2010 International Stroke Conference (23-25 Feb. 2010) held in San Antonio, Tex. and hosted by the American Stroke Association.

BRIEF SUMMARY OF THE INVENTION

It has now been found that a monoclonal anti-MAG antibody (herein Antibody A) is effective when administered intravenously in two doses for treating stroke in other models, such as in Squirrel Monkeys, and in humans. Therefore, anti-MAG antibodies, when administered in this way could provide benefit over existing therapies, such as tPA which is approved only for use within the first 3 hours post-stroke. By neutralizing over-expression of MAG in the peri-infarct area Antibody A may enhance survival of jeopardized, but not irreversibly injured neurons (e.g. via oligodendrocyte protection and neuro-regeneration) and may enhance plasticity of surviving neurons.

In one aspect, the present invention provides an anti-MAG antibody for use in the treatment of stroke wherein the antibody is administered intravenously in two doses and wherein,
 i) the first dose of antibody is administered up to 3 days after the onset of stroke (post-stroke); and
 ii) the second dose of antibody is administered between 3 and 10 days after the first dose.

In a second aspect, the invention provides a method of treating stroke comprising intravenous administration of an anti-MAG antibody to a human patient in need thereof in two doses and wherein,
 i) the first dose of antibody is administered up to 3 days after the onset of stroke (post-stroke); and
 ii) the second dose of antibody is administered between 3 and 10 days after the first dose.

In a third aspect, the invention provides the use of an anti-MAG antibody in the manufacture of a medicament for the treatment of stroke, wherein the antibody is administered intravenously in two doses and wherein, i) the first dose of antibody is administered up to 3 days after the onset of stroke (post-stroke); and ii) the second dose of antibody is administered between 3 and 10 days after the first dose.

In a fourth aspect, the present invention provides an anti-MAG antibody for use in the treatment of stroke wherein the anti-MAG antibody provides an $AUC_{(0\text{-}inf)}$ value of between 0.9-517.8 mg/mL h or of between 0.9-517.8 mg/mL h±10% as determined by the calculation and methods disclosed in Example 8.

In a fifth aspect, the present invention provides a method of treating stroke comprising administering an effective amount of an anti-MAG antibody to a human patient, and wherein the anti-MAG antibody provides an $AUC_{(0\text{-}inf)}$ value of between 0.9-517.8 mg/mL h or of between 0.9-517.8 mg/mL h±10% as determined by the calculation and methods disclosed in Example 8.

In a sixth aspect, the present invention provides the use of an anti-MAG antibody in the manufacture of a medicament for the treatment of stroke, wherein the anti-MAG antibody provides an $AUC_{(0\text{-}inf)}$ value of between 0.9-517.8 mg/mL h or of between 0.9-517.8 mg/mL h±10% as determined by the calculation and methods disclosed in Example 8.

In a seventh aspect, the present invention provides an anti-MAG antibody for use in the treatment of stroke wherein the anti-MAG antibody provides a $C_{max}$ value of between 3.0-1666.8 µg/mL or of between 3.0-1666.8 µg/mL±10% as determined by the calculation and methods disclosed in Example 8.

In an eighth aspect, the present invention provides a method of treating stroke comprising administering an effective amount of an anti-MAG antibody to a human patient, and wherein the anti-MAG antibody provides a $C_{max}$ value of between 3.0-1666.8 µg/mL or of between 3.0-1666.8 µg/mL±10% as determined by the calculation and methods disclosed in Example 8.

In a ninth aspect, the present invention provides the use of an anti-MAG antibody in the manufacture of a medicament for the treatment of stroke, wherein the anti-MAG antibody provides a $C_{max}$ value of between 3.0-1666.8 µg/mL or of between 3.0-1666.8 µg/mL±10% as determined by the calculation and methods disclosed in Example 8.

Other aspects and advantages of the present invention are described further in the claims, detailed description and the embodiments thereof.

DETAILED DESCRIPTION ON THE INVENTION

Figure 1:
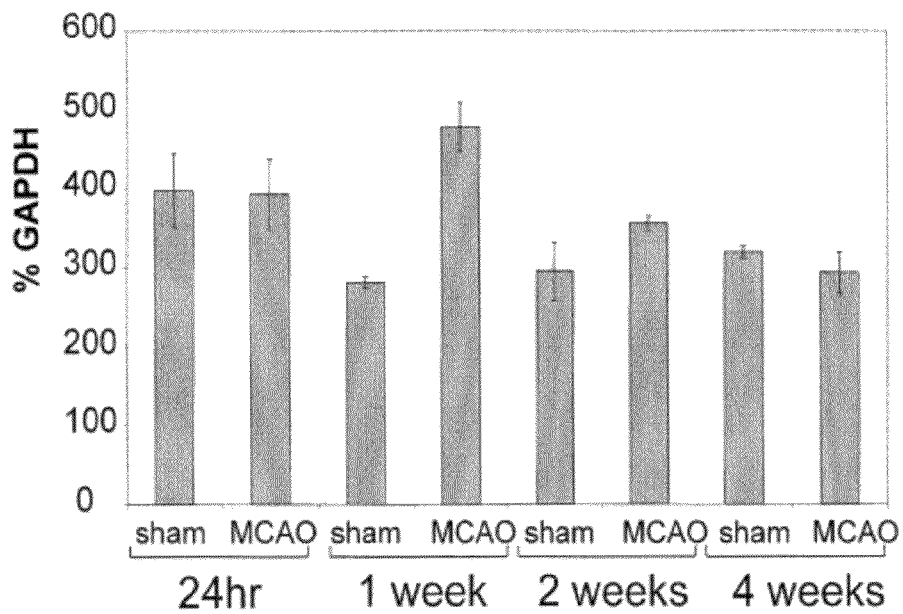
FIG. 1: mRNA levels in the cerebral cortex following transient MCAO in the rat.

Diseases which may be treated by the methods of the present invention include stroke, such as hemorrhagic and ischemic stroke.

It has now been found that a monoclonal anti-MAG antibody ("Antibody A"), as described in PCT application PCT/EP2003/008749 (published as WO2004/014953 A2) and PCT application PCT/EP2004/001016 (published as WO2004/083363 A2), when administered intravenously in two doses following focal cerebral ischaemia in the rat (a model of stroke) results in an improvement in clinical endpoints.

The antibody useful in the invention may be a fully human antibody or an altered antibody, such as a monoclonal antibody (mAb) or may be engineered, e.g. chimeric, humanised or reshaped. In one embodiment, the antibody is humanised. For further information on the types and structure of antibodies contemplated for use in the present invention, see PCT application PCT/EP2004/001016 (published as WO2004/083363 A2) page 3, line 7 to page 12, line 23.

In one aspect of the present invention, the antibody useful in the present invention is class IgG, such as IgG1. In one embodiment, the antibody is humanised.

The antibody useful in the present invention binds to human MAG and may comprise one or more of the following CDRs. The CDRs are identified as described by Kabat (Kabat et al., 1991, "Sequences of proteins of immunological interest", Fifth Edition, US Department of Health and Human Services, NIH publication No 91-3242). CDRs are typically as defined by Kabat, but following the principles of protein structure and folding as defined by Chothia and Lesk, (Chothia et al., 1989, "Conformations of immunoglobulin hypervariable regions", Nature, 342, p 877-883), it will be appreciated that additional residues may also be considered to be part of the antigen binding region and are thus encompassed by the antibodies useful in the present invention.

| Light chain CDRs | | |
|---|---|---|
| CDR | According to Kabat | |
| L1 | KSSHSVLYSSNQKNYLA | (Seq ID No 1) |
| L2 | WASTRES | (Seq ID No 2) |
| L3 | HQYLSSLT | (Seq ID No 3) |
| Heavy chain CDRs | | |
| CDR | According to Kabat | |
| H1 | NYGMN | (Seq ID No 4) |
| H2 | WINTYTGEPTYADDFTG | (Seq ID No 5) |
| H3 | NPINYYGINYEGYVMDY | (Seq ID No 6) |

In one embodiment, the altered antibody useful in the present invention comprises a heavy chain variable domain which comprises one or more CDRs selected from CDRH1, CDRH2 and CDRH3 and a light chain variable domain which comprises one or more CDRs selected from CDRL1, CDRL2 and CDRL3.

In another embodiment, the altered anti-MAG antibody thereof useful in the present invention comprises:

a) a heavy chain variable domain ($V_H$) which comprises in sequence CDRH1, CDRH2 and CDRH3, and/or b) a light chain variable domain ($V_L$) which comprises in sequence CDRL1, CDRL2 and CDRL3.

Seq ID No 7 is the sequence of a mouse/human chimeric anti-MAG antibody heavy chain in which the murine anti-MAG heavy chain variable region is associated with a functional immunoglobulin secretion signal sequence, and with an altered form of the human IgG1 constant region, in which Kabat residues 248 and 250 have been mutated to alanine in order to disable the effector functions of binding to FcγRI and complement protein C1q (Duncan, A. R. and Winter, G. Localization of the C1q binding site on antibodies by surface scanning. Duncan, A. R., Woolf, J. M., Partridge, L. J., Burton, D. R. and Winter, G., Nature, v332, p 738-740, 1988.

(Seq ID No 7)
MGWSCIILFLVATATGVHSEIQLVQSGPELKKPGETNKISCKASGYTFTNYGMNWVKQAPGKGLKW

MGWINTYTGEPTYADDFTGRFAFSLETSASTAYLQISNLKNEDTATYFCARNPINYYGINYEGYVM

DYWGQGTLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCPAPELAG

APSVFLFPPKPKDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHEALHN

HYTQKSLSLSPGK

Seq ID No 8 is a sequence of a mouse/human chimeric anti-MAG antibody light chain in which the murine anti-MAG light chain variable region is associated with a functional immunoglobulin secretion signal sequence, and with the human kappa constant region.

(Seq ID No 8)
MGWSCIILFLVATATGVHSNIMMTQSPSSLAVSAGEKVTMSCKSSHSVLYSSNQKNYLAWYQQKPG

QSPKLLIYWASTRESGVPDRFTGSGSGTDFTLTIINVHTEDLAVYYCHQYLSSLTFGTGTKLEIKR

TVAAPSVFIFPPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC

Seq ID No 9 is a sequence of a mouse/human chimeric anti-MAG antibody heavy chain which provides the amino acid sequence of a chimeric immunoglobulin heavy chain in which the murine anti-MAG heavy chain variable region is associated with a functional immunoglobulin secretion signal sequence, and with a wild-type type form of the human IgG1 constant region.

(Seq ID No 9)
MGWSCIILFLVATATGVHSEIQLVQSGPELKKPGETNKISCKASGYTFTNYGMNWVKQAPGKGLKW

MGWINTYTGEPTYADDFTGRFAFSLETSASTAYLQISNLKNEDTATYFCARNPINYYGINYEGYVM

DYWGQGTLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCPAPELLG

GPSVFLFPPKPKDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHEALHN

HYTQKSLSLSPGK

Thus, for example, an altered antibody useful i the present invention includes an altered antibody comprising a heavy chain Seq ID No 9 or 7 and/or a light chain Seq ID No 8.
In a further embodiment, the antibody for use in the present invention is a humanised antibody that binds to MAG and comprises a heavy chain variable region comprising the following amino acid sequences (Seq ID No 10-13):

(Seq ID No 10)
QVQLVQSGSELKKPGASVKVSCKASGYTFTNYGMNWVRQAPGQGLEWMGWINTYTGEPTYADDFTGRF

VFSLDTSVSTAYLQISSLKAEDTAVYYCARNPINYYGINYEGYVMDYWGQGTLVTVSS (Seq ID No 11)
QVQLVQSGSELKKPGASVKVSCKASGYTFTNYGMNWVRQAPGQGLEWMGWINTYTGEPTYADDFTGRF

VFSLDTSVSTAYLQISSLKAEDTAVYFCARNPINYYGINYEGYVMDYWGQGTLVTVSS (Seq ID No 12)
QVQLVQSGSELKKPGASVKVSCKASGYTFTNYGMNWVRQAPGQGLEWMGWINTYTGEPTYADDFTGRF

VFSLDTSVSTAYLQISSLKAEDTATYFCARNPINYYGINYEGYVMDYWGQGTLVTVSS (Seq ID No 13)
QVQLVQSGSELKKPGASNKVSCKASGYTFTNYGMNWVRQAPGQGLEWMGWINTYTGEPTYADDFTGRF

VFSLDTSVSTAYLQISSLKAEDTATYFCARNPINYYGINYEGYVMDYWGQGTLVTVSS

In each of these cases each of the 4 heavy chains may be combined with one of four light chain variable regions (Seq ID No 14-17):

(Seq ID No 14)
DIVMTQSPDSLAVSLGERATINCKSSHSVLYSSNQKNYLAWYQQKPGQPPKLLIYWASTRESGVPDRFSG

SGSGTDFTLTISSLQAEDVAVYYCHQYLSSLTFGQGTKLEIKRTV

-continued (Seq ID No 15)
DIVMTQSPDSLAVSLGERATINCKSSHSVLYSSNQKNYLAWYQQKPGQPPKLLIYWASTRESGVPDRFSG

SGSGTDFTLTIINLQAEDVAVYYCHQYLSSLTFGQGTKLEIKRTV (Seq ID No 16)
DIVMTQSPDSLAVSLGERATINCKSSHSVLYSSNQKNYLAWYQQKPGQPPKLLIYWASTRESGVPDRFSG

SGSGTDFTLTISSLHTEDVAVYYCHQYLSSLTFGQGTKLEIKRTV (Seq ID No 17)
DIVMTQSPDSLAVSLGERATINCKSSHSVLYSSNQKNYLAWYQQKPGQPPKLLIYWASTRESGVPDRFSG

SGSGTDFTLTIINLHTEDVAVYYCHQYLSSLTFGQGTKLEIKRTV

Antibodies for use in the present invention therefore include all combinations of embodiments listed above. In particular, antibodies useful in the present invention include all combinations of each of the above 4 heavy chains (Seq ID No 10-13) with each of the 4 light chains (Seq ID No 14-17).

One exemplary antibody useful in the present invention comprises a mature heavy chain comprising the amino acid sequence of Seq ID No 18 and a mature light chain comprising the amino acid sequence of Seq ID No. 19 (see below), herein referred to as "Antibody A".

[Seq ID No 18]
QVQLVQSGSELKKPGASVKVSCKASGYTFTNYGM

NWVRQAPGQGLEWMGWINTYTGEPTYADDFTGRFVFSLDTSVSTAYLQI

SSLKAEDTAVYYCARNPINYYGINYEGYVMDYWGQGTLVTVSSASTKGP

SVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCD

KTHTCPPCPAPELAGAPSVFLFPPKPKDTLMISRTPEVTCVVVDVSHED

PEVKFNWYVDGVEVHNAKTKPREEQYNSTYRWSVLTVLHQDWLNGKEYK

CKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQ

QGNVFSCSVMHEALHNHYTQKSLSLSPGKDIVMTQSPDSLAVSLGERAT

INCKSSHSVLYSSN

[Seq ID No 19]
QKNYLAWYQQKPGQPPKLLIYWASTRESGVPDRFSGSGSGTDFTLTISS

LQAEDVAVYYCHQYLSSLTFGQGTKLEIKRTVAAPSVFIFPPSDEQLKS

GTASVVCLLNNFYPREAKVQWKVDNALQSGNSQESVTEQDSKDSTYSLS

STLTLSKADYEKHKVYACEVTHQGLSSPVTKSFNRGEC

Definitions

Antibodies useful in the present invention encompass "altered antibodies", "engineered antibodies", "chimeric antibodies", "humanized antibodies" and "reshaped human antibodies". These terms are to be interpreted as defined in PCT application PCT/EP2004/001016 (published as WO2004/083363 A2) page 9, line 16 to page 13, line 12.

"CDRs" are defined as the complementarity determining region amino acid sequences of an antibody which are the hypervariable regions of immunoglobulin heavy and light chains. See, for example, Kabat et al., "Sequences of Proteins of Immunological Interest", 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See, for example, Chothia et al., (1989), "Conformations of immunoglobulin hypervariable regions", Nature, 342, p 877-883.

CDRs provide the majority of contact residues for the binding of the antibody to the antigen or epitope. CDRs of interest for use in this invention are derived from donor antibody variable heavy and light chain sequences, and include analogs of the naturally occurring CDRs, which analogs also share or retain the same antigen binding specificity and/or neutralizing ability as the donor antibody from which they were derived. The term "analog" is to be interpreted as defined in PCT application PCT/EP2004/001016 (published as WO2004/083363 A2) page 12, line 30 to page 13, line 12.

As used herein, "maximum plasma concentration" or "$C_{max}$" means the highest observed concentration of a substance (for example, an anti-MAG antibody) in mammalian plasma after administration of the substance to the mammal.

As used herein, "Area Under the Curve" or "AUC" is the area under the curve in a plot of the concentration of a substance (for example, an anti-MAG antibody) in plasma against time. AUC can be a measure of the integral of the instantaneous concentrations during a time interval and has the units mass×time/volume. AUC is typically calculated by the non-compartmental method (e.g. the trapezoidal method, such as linear or linear-log), or by the compartmental method. AUC is usually given for the time interval zero to infinity, and other time intervals are indicated (for example $AUC_{(t1,t2)}$ where t1 and t2 are the starting and finishing times for the interval). Thus, as used herein "$AUC_{(0-inf)}$" refers to AUC from t=0, over an infinite time period.

As used herein, "$T_{max}$" refers to the observed time for reaching the maximum concentration of a substance in plasma of a mammal after administration of that substance to the mammal.

As used herein, "serum or plasma half life" refers to the time required for half the quantity of a substance administered to a mammal to be metabolized or eliminated from the serum or plasma of the mammal by normal biological processes.

As used herein, "mean plasma concentration" refers to the mean of the observed concentrations in a group of subjects at each time point or, when referring to a compartmental analysis in a population of subjects in a simulation, to the typical profile obtained from the population parameters of the used compartmental model.

Construction and Production of Antibodies

A neutralising antibody specific for MAG has been described (Poltorak et al., (1987), *Journal of Cell Biology*, 105, 1893-1899; DeBellard et al., (1996), *Mol. Cell. Neurosci.*, 7, 89-101; Tang et al., (1997), *Mol. Cell. Neurosci.*, 9, 333-346; Torigoe K and Lundborg G, (1997), *Exp. Neurology*, 150, 254-262) and is also commercially available (MAB1567 (Chemicon)). Other anti-MAG antibodies are also described in PCT application PCT/EP2004/001016 (published as WO2004/083363 A2), PCT application PCT/EP2003/008749 (published as WO2004/014953 A2) and PCT application PCT/GB2002/000551 (published as WO2002/062383 A2).

Methods for making antibodies for use in the present invention are described in PCT application PCT/EP2004/001016 (published as WO2004/083363 A2) page 13, line 29 to page 21, line 18.

A conventional expression vector or recombinant plasmid is produced by placing coding sequences for the antibody in operative association with conventional regulatory control sequences capable of controlling the replication and expression in, and/or secretion from, a host cell. Regulatory sequences include promoter sequences, e.g. CMV promoter, and signal sequences, which can be derived from other known antibodies. Similarly, a second expression vector can be produced, having a DNA sequence which encodes a complementary antibody light or heavy chain. This second expression vector may be identical to the first except insofar as the coding sequences and selectable markers are concerned, so to ensure as far as possible that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell comprising both the recombinant or synthetic light and heavy chains. The transfected cell is then cultured by conventional techniques to produce the engineered antibody useful in the present invention. The humanized antibody which includes the association of both the recombinant heavy chain and/or light chain is screened from culture by appropriate assay, such as ELISA or RIA. Similar conventional techniques may be employed to construct other altered antibodies and molecules.

Suitable vectors for the cloning and subcloning steps employed in the methods and construction of the compositions useful in this invention may be selected by one of skill in the art. For example, the conventional pUC series of cloning vectors, may be used. One vector, pUC19, is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor.

Similarly, the vectors employed for expression of the antibodies may be selected by one of skill in the art from any conventional vector. The vectors also contain selected regulatory sequences (such as CMV promoters) which direct the replication and expression of heterologous DNA sequences in selected host cells. These vectors contain the above described DNA sequences which code for the antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g. the mammalian dihydrofolate reductase gene (DHFR). Other vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

Cell lines transfected with a recombinant plasmid containing the coding sequences of the antibodies or altered immunoglobulin molecules thereof are useful for making the antibodies useful in the present invention. Host cells useful for the cloning and other manipulations of these cloning vectors are also conventional. However, most desirably, cells from various strains of *E. coli* are used for replication of the cloning vectors and other steps in the construction of altered antibodies useful in the present invention.

Suitable host cells or cell lines for the expression of the antibodies useful in the present invention include mammalian cells such as NS0, Sp2/0, CHO, COS, a fibroblast cell (e.g. 3T3), and myeloma cells, and in one embodiment is a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Where desired, strains of yeast cells known to those skilled in the art are also available as host cells, as well as insect cells, e.g. *Drosophila* and *Lepidoptera* and viral expression systems. See, e.g. Miller et al., "Genetic Engineering", 8:277-298, Plenum Press (1986) and references cited therein.

The skilled person will appreciate that, upon production of the antibody, in particular depending on the cell line used and particular amino acid sequence of the antibody, post-translational modifications may occur. For example, this may include the cleavage of certain leader sequences, the addition of various sugar moieties in various glycosylation patterns, deamidation, oxidation, disulfide bond scrambling, isomerisation, C-terminal lysine clipping, and N-terminal glutamine cyclisation. The present invention encompasses the use of antibodies which have been subjected to, or have undergone, one or more post-translational modifications.

Deamidation is an enzymatic reaction primarily converting asparagine (N) to iso-aspartic acid and aspartic acid (D) at approximately 3:1 ratio. To a much lesser degree, deamidation can occur with glutamine residues in a similar manner. Deamidation in a CDR results in a change in charge of the molecule, but typically does not result in a change in antigen binding, nor does it impact on PK/PD.

Oxidation can occur during production and storage (i.e. in the presence of oxidizing conditions) and results in a covalent modification of a protein, induced either directly by reactive oxygen species or indirectly by reaction with secondary byproducts of oxidative stress. Oxidation happens primarily with methionine residues, but occasionally can occur at tryptophan and free cysteine residues.

Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling.

Isomerization typically occurs during production, purification, and storage (at acidic pH) and usually occurs when aspartic acid is converted to isoaspartic acid through a chemical process.

N-terminal glutamine in the heavy chain and/or light chain is likely to form pyroglutamate (pGlu). Most pGlu formation happens in the production bioreactor, but it can be formed non-enzymatically, depending on pH and temperature of processing and storage conditions. pGlu formation is considered as one of the principal degradation pathways for recombinant mAbs.

C-terminal lysine clipping is an enzymatic reaction catalyzed by carboxypeptidases, and is commonly observed in recombinant mAbs. Variants of this process include removal of lysine from one or both heavy chains. Lysine clipping does not appear to impact bioactivity and has no effect on mAb effector function.

The general methods by which the vectors may be constructed, the transfection methods required to produce host cells, and culture methods necessary to produce the altered antibody useful in the present invention from such host cell are all conventional techniques. Likewise, once produced, the antibodies useful in the present invention may be purified from the cell culture contents according to standard procedures of the art, including ammonium sulfate precipitation, affinity columns, column chromatography, gel electrophoresis and the like. Such techniques are within the skill of the art. For example, preparation of altered antibodies is described in WO99/58679 and WO96/16990.

Yet another method of expression of the antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

Once expressed by the desired method, the antibody is then examined for in vitro activity by use of an appropriate assay. Presently, conventional ELISA assay formats are employed to assess qualitative and quantitative binding of the antibody to MAG. Additionally, other in vitro assays may also be used to verify neutralizing efficacy prior to subsequent human clinical studies performed to evaluate the persistence of the antibody in the body despite the usual clearance mechanisms.

Dosing Schedule

It has been found that the dosing schedule as described in the claims may have a number of potential benefits, which include:

1) The demonstration that Antibody A can be administered as an intravenous infusion, rather than directly to the brain, (which is possible because of the ability of the antibodies to cross the blood brain barrier over a sustained period of time of up to 2 weeks) which markedly increases the feasibility of treatment in a fragile population where direct CNS administration may be detrimental;
2) Lower $C_{max}$, when compared to administration of single dose, which may result in fewer, or less severe side effects;
3) Improved efficacy due to continued maintenance of plasma drug levels through at least the period of increased MAG expression following stroke;
4) Improved timescale of administration as compared to the known therapy, tPA, which needs to be administered within the first 3 hours of the onset of stroke; and/or
5) Improved ability to select patients most likely to benefit from therapy, because the patients will no longer be in the acute period post-stroke and may be selected because they have a pre-determined deficit e.g. motor deficit, cognitive deficit, language deficit etc.

In the dosing regimen of the present invention, the first dose can be administered up to 3 days after the onset of stroke (post-stroke). In one embodiment, the first dose is administered on the first, second or third day post-stroke. In another embodiment, the first dose is administered between 1 and 2 days post-stroke. Alternatively, the first dose of anti-MAG antibody is administered up to 72 hours after the onset of stroke (post-stroke). In one embodiment, the first dose is administered between 12 and 72, or between 12 and 48 hours, or between 24 and 72 hours post-stroke. In another embodiment, the first dose is administered between 24 and 48 hours post-stroke.

The timing of the administration of the first dose of anti-MAG antibody will depend, in part, upon identification of the stroke in the patient and admitting them to hospital. One benefit of the present invention is that the antibody may be administered either during or after the acute period of stroke. One advantage of the presently claimed invention, over the marketed drug tPA is that tPA is authorised for administration within 3 hours post-stroke (i.e. in the acute period). In practice, this means that only a proportion of patients can receive therapy largely because the timing of the onset of stroke is not known (for example, if it occurred during sleep) and because of the requirement of a CT scan to exclude haemorrhagic stroke. A longer therapeutic window would therefore be beneficial.

The second dose of anti-MAG antibody is administered between 3 and 10 days after the first dose. In one embodiment, the second dose is administered between 3 and 7 days, or 4 and 9 days, or 5 and 8 days or 6 and 7, or 8 and 10 days after the first dose. In another embodiment, the second dose is administered on day 3, 4, 5, 6, 7, 8, 9 or 10 after the first dose.

The timing of the administration of the second dose of anti-MAG antibody is designed primarily to maximise efficacy, whilst reducing the risk of the occurrence of side-effects. In administering the antibody split over two doses, we have shown in simulation studies that the overall $C_{max}$ can be reduced, while maintaining the area under the curve (AUC), see Examples 8 and 9. Furthermore, it is expected that, because the permeability of the BBB has been shown to still be compromised over a two week period following stroke, the amount of systemic exposure to the antibody is reduced, and smaller amounts of drug can be administered, increasing the cost-effectiveness of the treatment. It has also been observed that the expression of MAG in the brain continues increasing after stroke (see Example 3), and it has been shown that an anti-MAG antibody useful in the present invention co-localises with the MAG protein in the penumbra of the brain (See Example 5). We hypothesize that the second dose of antibody maintains efficacious plasma levels and corresponds to the time period during which MAG levels are expressed in the brain, and when brain regeneration/sprouting and synaptic plasticity is known to occur.

Pharmacodynamic parameters, such as AUC, $C_{max}$ and mean plasma concentrations, may also be used to define the present invention. A skilled artisan will understand the various methods for measuring and calculating the pharmacokinetic (for example, but not limited to, $C_{max}$, AUC, $T_{max}$, plasma half-life, mean plasma concentration) and pharmacodynamic (for example, but not limited to, MAG levels) parameters described herein. Furthermore, the skilled artisan will understand the various methods for making statistical comparisons (for example, but not limited to, comparisons of change from baseline to post-treatment and/or comparisons among treatment groups) and/or analysis of the pharmacokinetic and pharmacodynamic parameters described herein, see for illustrative purposes Example 8 and 9 below.

Hence, in one embodiment, there is provided an anti-MAG antibody for use in the treatment of stroke wherein the anti-MAG antibody provides an $AUC_{(0-inf)}$ value of between 0.9-517.8 mg/mL h as determined by the calculation and methods disclosed in Example 8, such as between 8.4-281.2, between 8.4-21.8, or between 47.7-93.5, or between 166.9-281.2 mg/mL h. Exemplary values of $AUC_{(0-inf)}$ are approximately 13.6, approximately 66.8 or approximately 216.6 mg/mL h as determined by the calculation and methods disclosed in Example 8. In another embodiment, all of these values and ranges may be ±10%.

In another embodiment, there is provided a method of treating stroke comprising administering an effective amount of an anti-MAG antibody to a human patient, and wherein the anti-MAG antibody provides an AUC value of between 0.9-517.8 mg/mL h as determined by the calculation and methods disclosed in Example 8, such as between 8.4-281.2, between 8.4-21.8, or between 47.7-93.5, or between 166.9-281.2 mg/mL h. Exemplary values of $AUC_{(0-inf)}$ are approximately 13.6, approximately 66.8 or approximately 216.6 mg/mL h as determined by the calculation and methods disclosed in Example 8. In another embodiment, all of these values and ranges may be ±10%.

In another embodiment, there is provided the use of an anti-MAG antibody in the manufacture of a medicament for the treatment of stroke, wherein the anti-MAG antibody provides an AUC value of between 0.9-517.8 mg/mL h as determined by the calculation and methods disclosed in Example 8, such as between 8.4-281.2, or between 8.4-21.8, or between 47.7-93.5, or between 166.9-281.2 mg/mL h. Exemplary values of $AUC_{(0-inf)}$ are approximately 13.6, approximately 66.8 or approximately 216.6 mg/mL h as determined by the calculation and methods disclosed in Example 8. In another embodiment, all of these values and ranges may be ±10%.

In a further embodiment, there is provided an anti-MAG antibody for use in the treatment of stroke wherein the anti-MAG antibody provides a $C_{max}$ value of between 3.0-1666.8 µg/mL as determined by the calculation and methods disclosed in Example 8, such as between 27.7-1142.2, or between 27.7-93.1, or between 164.4-278.5, or between 480.3-1142.2 µg/mL. Exemplary values of $C_{max}$ are approximately 50.8, approximately 213.9 or approximately 740.6 µg/mL as determined by the calculation and methods disclosed in Example 8. In another embodiment, all of these values and ranges may be ±10%.

In another embodiment, there is provided a method of treating stroke comprising administering an effective amount of an anti-MAG antibody to a human patient, and wherein the anti-MAG antibody provides a $C_{max}$ value of between 3.0-1666.8 µg/mL as determined by the calculation and methods disclosed in Example 8, such as between 27.7-1142.2, or between 27.7-93.1, or between 164.4-278.5, or between 480.3-1142.2 µg/mL. Exemplary values of $C_{max}$ are approximately 50.8, approximately 213.9 or approximately 740.6 µg/mL as determined by the calculation and methods disclosed in Example 8. In another embodiment, all of these values and ranges may be ±10%.

In another embodiment, there is provided the use of an anti-MAG antibody in the manufacture of a medicament for the treatment of stroke, wherein the anti-MAG antibody provides a $C_{max}$ value of between 3.0-1666.8 µg/mL as determined by the calculation and methods disclosed in Example 8, such as between 27.7-1142.2, or between 27.7-93.1, or between 164.4-278.5, or between 480.3-1142.2 µg/mL. Exemplary values of $C_{max}$ are approximately 50.8, approximately 213.9 or approximately 740.6 µg/mL as determined by the calculation and methods disclosed in Example 8. In another embodiment, all of these values and ranges may be ±10%.

In another embodiment, the antibody, method or use described above has both the $AUC_{(0-inf)}$ value (or range) and the $C_{max}$ value (or range), which values and ranges of values are described above.

Composition

The antibodies useful in the present invention are usually administered in an aqueous composition.

Pharmaceutical compositions contain an effective amount of the antibody useful in the present invention as an active ingredient. In one aspect, an aqueous solution containing the antibody, which may be buffered at physiological pH, in a form ready for injection is prepared. The compositions will commonly comprise a solution of an anti-MAG antibody dissolved in a pharmaceutically acceptable carrier, which is typically an aqueous carrier or diluent. A variety of aqueous carriers may be employed, e.g. 0.9% saline, and the like. The aqueous component of the compositions useful in the present invention is typically a high grade quality of water such as water for injection. These solutions are sterile and generally free of particulate matter. The solutions may be sterilized by conventional, well known sterilization techniques (e.g. filtration). Compositions may contain pharmaceutically acceptable auxiliary substances, as required, to approximate physiological conditions such as pH adjusting and buffering agents, etc.

The skilled person would readily appreciate that some auxiliary substances may perform more than one function, depending on the nature and number of auxiliary substances used in that composition and the particular properties of the drug contained therein.

One or more tonicity adjusting agent(s) may be included to achieve isotonicity with body fluids e.g. with the blood or skin, which may result in reduced levels of irritancy. Examples of pharmaceutically acceptable tonicity adjusting agents include, but are not limited to, sodium chloride, dextrose, xylitol and calcium chloride. In one embodiment, the composition includes a tonicity adjusting agent which is sodium chloride.

The compositions useful in the present invention may be buffered by the addition of suitable buffering agents such as sodium acetate (which may be hydrated, e.g. as the trihydrate), sodium citrate, citric acid, trometarol, phosphates such as disodium phosphate (for example the dodecahydrate, heptahydrate, dihydrate and anhydrous forms) or sodium phosphate and mixtures thereof. In one embodiment, the composition includes a buffering agent which is sodium acetate. In another embodiment, the buffering agent is sodium acetate trihydrate.

Compositions may include one or more stabilising agents for both preventing surface adsorption and as stabilizers against protein aggregation due to denaturation at interfaces like liquid/air and liquid/container interfaces. Examples of pharmaceutically acceptable stabilising agents include, but are not limited to, fatty alcohols, esters and ethers, such as polyoxyethylene (80) sorbitan monooleate (Polysorbate 80), macrogol ethers and poloxamers. In one embodiment, the composition includes a stabilising agent which is polyoxyethylene (80) sorbitan monooleate (Polysorbate 80).

Chelating agents such as disodium ethylenediaminetetraacetate (EDTA) effectively scavenge free metal ions in a solution before they oxidize the proteins and may be used to inhibit metal catalyzed oxidation. In one embodiment, the composition includes a chelating agent which is disodium ethylenediaminetetraacetate (EDTA).

Solubility enhancers such as arginine have now become very important solvent additives for the enhancement of protein solubility and suppression of protein aggregation. In one embodiment, the composition includes a solubilizer which is an arginine base.

The concentration of the antibody useful in the present invention in such pharmaceutical composition can vary widely, i.e. from about 15 to 150 mg/mL, e.g. about 50 to 150 mg/mL, such as about 60 to 140 mg/mL, e.g. about 70 to 130 mg/mL, for example about 80 to 120 mg/mL. In one embodiment, the concentration of antibody in the composition is from about 90 to 115 mg/mL, or about 90 to 110 mg/mL. Drug concentrations will generally be selected primarily based on fluid volumes, viscosities, etc., as required.

In one embodiment, the aqueous composition comprises an anti-MAG antibody useful in the present invention and sodium acetate, sodium chloride and Polysorbate 80. In another embodiment, the aqueous composition comprises 50 mM sodium acetate, 104.4 mM sodium chloride and 0.02% by weight Polysorbate 80. In another embodiment, the aqueous composition comprises an anti-MAG antibody useful in the present invention and sodium acetate, arginine, EDTA, sodium chloride and Polysorbate 80. In another embodiment, the aqueous composition comprises 25-75 mM sodium acetate, 75-125 mM sodium chloride and 0.005-0.01% by weight Polysorbate 80. In another embodiment, the aqueous composition comprises 25-75 mM sodium acetate, 25-75 mM sodium chloride, 0.5-2% by weight arginine, 0.03-0.07 mM EDTA and 0.005-0.01% by weight Polysorbate 80. In another embodiment, the aqueous composition comprises 50 mM sodium acetate, 51 mM sodium chloride, 1% by weight arginine, 0.05 mM EDTA and 0.02% by weight Polysorbate 80. In a further embodiment, the composition is pH adjusted to between 5 and 6. In a further embodiment, the pH of the composition is about 5.5. When the pH is adjusted, a suitable acid may be used, such as hydrochloric acid.

Actual methods for preparing parenterally administrable compositions are well known or will be apparent to those skilled in the art and are described in more detail in, for example, Remington's Pharmaceutical Science, 15th ed., Mack Publishing Company, Easton, Pa., as well as in the following examples.

In another embodiment, the antibodies for use in the invention, when in a pharmaceutical composition, are present in unit dose forms. The appropriate therapeutically effective dose can be determined readily by those of skill in the art. In the dosing regimen of the present invention, the dose administered to the patient on each occasion is from 0.1 mg/kg to 25 mg/kg. It is expected that the same dose will be administered to the patient on each occasion. In one embodiment, the dose administered to the patient on each occasion is selected from 1 mg/kg, 5 mg/kg and 15 mg/kg. A person skilled in the art will appreciate that, in order to minimise risk of side-effects and to maximise cost-effectiveness, the lowest efficacious dose should be selected. Hence in one embodiment, the dose administered to the patient on each occasion is selected from 0.1 mg/kg, 0.2 mg/kg, 0.3 mg/kg, 0.4 mg/kg, 0.5 mg/kg, 0.6 mg/kg, 0.7 mg/kg, 0.8 mg/kg and 0.9 mg/kg.

The antibodies useful in the present invention may be administered by intravenous infusion. In one embodiment, the antibody is infused over a period of up to 60 min. Alternatively, the drug may be administered over a period of up to 120 minutes, such as up to 90 min, 60 min, 45 min, 30 min or 15 min.

The antibodies described herein can be lyophilized for storage and reconstituted in a suitable carrier prior to use. This technique has been shown to be effective with conventional immunoglobulins and art-known lyophilization and reconstitution techniques can be employed. Alternatively, the antibodies can be stored in a more concentrated solution ("stock solution"), as compared to the concentration which will be administered. In one embodiment, stock solutions are at a concentration of 100 mg/mL of antibody. Typically, the solution will be kept in a suitable vial, such as one made of glass. In one embodiment, the vial holds a total volume of 10 mL of stock solution.

Exemplary compositions for use in the present method of treatment are shown below in tables 1 and 2.

TABLE 1

Formulation for clinical use

| Ingredient | Quantity per 10 mL | Function |
|---|---|---|
| Antibody A | 1000 mg | Active ingredient (drug) |
| Sodium acetate trihydrate | 68.1 mg | Buffer |
| Polysorbate 80 | 2.0 mg | Stabiliser |
| Sodium chloride | 61.0 mg | Tonicity adjuster |
| Hydrochloric acid | qs to give pH 5.5 | pH adjuster |
| Water for Injections | To make 10.0 mL | Vehicle |
| Nitrogen | to flush headspace | Processing aid |

TABLE 2

Formulation for non-clinical use

| Ingredient | Quantity per 1 mL | Function |
|---|---|---|
| Antibody A | 100 mg | Active ingredient (drug) |
| Sodium acetate trihydrate | 6.81 mg | Buffer |
| Disodium edetate dihydrate | 0.0186 mg | Chelating agent |
| Polysorbate 80 | 0.20 mg | Stabiliser |
| Arginine base | 10.00 mg | Solubiliser |
| Sodium chloride | 3.00 mg | Tonicity adjuster |
| Hydrochloric acid | qs to give pH 5.5 | pH adjuster |
| Water for Injections | To make 1.0 mL | Vehicle |
| Nitrogen | to flush headspace | Processing aid |

The following examples illustrate the invention. In vivo and in vitro data on the anti-MAG antibodies useful in the present invention are presented in Examples 1 to 5 of PCT application PCT/EP2004/001016 (published as WO2004/083363 A2). An exemplary antibody for administration in the methods of the present invention (Antibody A) may be prepared as described in Example 4 of PCT application PCT/EP2004/001016 (published as WO2004/083363 A2).

Example 1

Aqueous Composition for Intravenous Administration (Stock Solution)

Formulation Buffer Compounding

The compounding, formulation and fill are carried out at controlled ambient conditions. 1% Polysorbate 80 stock solution is prepared in a glass container. The solution is mixed for 20 min. The remaining excipients are weighed, as required. A compounding vessel is filled to approximately 75% of the bulk solution volume with Water for Injection (WFI). The weighed excipients are added individually with sodium acetate added first and polysorbate 80 stock solution added last to the compounding vessel with continuous mixing. The solution is mixed for at least 15 min. pH is adjusted with hydrochloric acid. WFI is added to bring the solution to its final weight and then the solution is mixed for at least 10 min.

Dilution of Drug Substance (DS) to Formulated Bulk

DS is removed from 2-8° C. storage at least 1 hour before dilution to allow the solution to equilibrate at ambient (room temperature). The BDS solution is brought to its final Batch size as calculated below with formulation buffer prepared above. Solution is gently mixed for at least 10 min.

Total Batch size (kg) =

$$\frac{DS \text{ (kg)}}{DS \text{ density}} \times \frac{DS \text{ concentration (mg/mL)}}{\text{Target concentration (mg/mL)}} \times \text{Drug Product density}$$

Preparation for Stock Solution

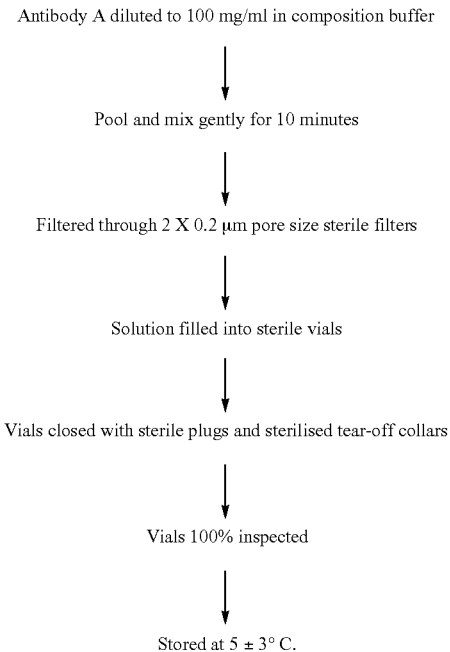

Drug substance pooling occurs at the drug product manufacturing site prior to sterile filtration. The drug substance from individual containers is pooled together and mixed gently at typical agitator speeds of 150-300 rpm for a minimum of 5 min. The mixing is monitored visually to verify that foaming is kept to a minimum while ensuring adequate movement of liquid throughout the container. The mixing is conducted at controlled ambient temperature which is controlled between 17-25° C. The pooled bulk drug substance is then filtered through 2×0.2 micron pore size sterile filters before filling into the drug product vials.

Example 2

Dilution of Aqueous Composition for Intravenous Administration

Dilution of Stock Solution for IV Infusion—Method 1

Preparation of X mg/kg dose of drug solution for administration. These calculations assume a 10 mL overfill in the IV bags; however, they may be applied as written even if an I.V. bag has a smaller overfill volume:

1. Using a 100 mL infusion bag or bottle as specified above, withdraw (2X+10) mL of 0.9% sodium chloride and discard it.
2. Withdraw a total of 2×mL of drug from stock solution and inject it into the 100 mL bag. This will provide a drug concentration in the infusion bag of 2× mg/mL.
3. Gently mix the solution in the bag by inverting the bag a couple of times
4. Calculate the volume to be administered to a subject using the following formula:

$$\frac{X \text{ mg/kg} \times subjectweight \text{ (kg)}}{2X \text{ mg/ml}} = \text{volume to be infused}$$

Example for X=15 mg/kg and 70 kg subject:

$$\frac{15 \text{ mg/kg} \times 70 \text{ kg}}{30 \text{ mg/mL}} = 35 \text{ mL}$$

5. Remove the excess volume from the bag, e.g. if the dose volume calculated is 35 mL, remove 65 mL from the bag. At this stage, optionally pull the 10 mL aliquot to be saved from the excess solution which is removed from the bag.
6. Deliver the entire bag to the patient. An additional flush volume of 30 mL saline must be delivered after administration of the entire bag in order to clear the lines of any drug substance and to ensure the full dose is administered. This additional volume should be administered via the volumetric pump to ensure the appropriate infusion rate is used. Alternatively, it may be administered via a bolus flush. The entire dose, which includes the drug solution and the additional flush, should be delivered within 60 minutes.

Dilution of Stock Solution for IV Infusion—Method 2

Preparation of X mg/kg dose of drug solution for administration. These calculations assume a 10 mL overfill in the IV bags; however, they may be applied as written even if an I.V. bag has a smaller overfill volume:

1. Calculate the Drug product volume to be added to the I.V. bag using the following formula:

$$\frac{X \text{ mg/kg} \times subjectweight \text{ (kg)}}{DP \text{ concentration}} = DP \text{ volume to be added } (Y)$$

Example for X=15 mg/kg dose for 80 kg subject:

$$\frac{15 \text{ mg/kg} \times 80 \text{ kg}}{100 \text{ mg/mL}} = 12 \text{ mL}$$

2. Using a 100 mL infusion bag or bottle as specified above, withdraw (Y+10) mL of 0.9% sodium chloride and discard it.
3. Withdraw a total of Y mL of drug solution and inject it into the 100 mL bag. Gently mix the solution in the bag by inverting the bag a couple of times
4. If an aliquot needs to be removed from the bag to be retained as a sample, the above calculation in step 1 will be modified to correct for this withdrawal
5. Deliver the remaining contents of the bag to the patient An additional flush volume of 30 mL saline must be delivered after administration of the entire bag in order to clear the lines of any drug solution and to ensure the full dose is administered. This additional volume should be administered via the volumetric pump to ensure the appropriate infusion rate is used. Alternatively, it may be administered via a bolus flush. The entire dose, which includes drug solution and the additional flush, should be delivered within 60 minutes.

Example 3

Expression of MAG in the Brain Post-Stroke

Introduction

The duration of dosing required for any given drug is driven by the expression profile of the target in the relevant disease model or clinical condition. There is limited information available in the literature regarding MAG distribution following MCAO. The aim of the current study was therefore to investigate the distribution of MAG following MCAO in the rat.

Methods

MAG expression levels in Sprague Dawley rats following focal cerebral ischaemia (David Virley et al., "A Temporal MRI Assessment of Neuropathology After Transient Middle Cerebral Artery Occlusion in the Rat: Correlations With Behavior", *Journal of Cerebral Blood Flow & Metabolism*, (2000) 20, 563-582), was measured as described previously (Irving et al., "Increased cortical expression of the orexin-1 receptor following permanent middle cerebral artery occlusion in the rat", Neurosci Lett., 2002 (May), 10, 324(1):53-6). A separate cohort of animals was processed for immunohistochemical analysis as described previously (Irving E A et al., "Assessment of white matter injury following prolonged focal cerebral ischaemia in the rat", Acta Neuropathol, (2001) 102, 627-635). MAG was detected using commercially available anti-MAG antibody (MAB1567 (Chemicon)).

Results 24 h following MCAO, MAG mRNA levels remained similar to those in sham operated animals. However increased mRNA levels were detected 1 week following injury which then decreased 2-4 weeks after the onset of ischaemia (FIG. 1).

Immunohistochemical assessment of MAG demonstrated that MAG immunoreactivity was restricted to myelinated tracts throughout the brain in normal tissue. Following injury, MAG localisation was detected in the tissue immediately surrounding the lesion from 24 h to 2 weeks following MCAO. The levels of MAG immunohistochemistry then decreased 4 weeks following MCAO. It is unclear if this apparent increase in immunoreactivity reflects increased levels of MAG protein or increased accessibility to MAG due to the white matter damage present following ischemia.

Conclusions

The results of this study demonstrate that MAG expression is increased between 24 h and 2 weeks following transient MCAO in the rat. This correlates well with increased expression detected following permanent MCAO in the rat (Li et al., Neurobiology of Disease, 2006, 23:362-373) as well as the data presented in Example 5. Together, these data suggest that MAG expression is elevated for 2-3 weeks in the lesion penumbra following the onset of cerebral ischaemia regardless of the whether the occlusion is permanent or transient in nature. Furthermore, this data suggests that to gain optimal efficacy, anti-MAG antibody exposure in the CNS should be maintained at efficacious levels for at least 2-3 weeks post-stroke.

Example 4

Permeability of the Blood Brain Barrier Post-Stroke: Assessment of BBB Leakage Using Gadolinium Introduction It is known that the blood brain barrier (BBB) becomes compromised following cerebral ischemia in humans and rodent models. While there are a number of studies which qualitatively describe BBB leakage in rodent models of stroke using markers such as IgG, these studies mainly focus on the acute period following the onset of cerebral ischaemia (Karin E. Sandoval, Ken A. Witt, "Blood-brain barrier tight junction permeability and ischemic stroke", Neurobiology of Disease, 32, (2008), 200-219). Furthermore, there are no systematic studies designed to characterise and compare BBB leakage in the multiple different stroke models available to researchers assessing the potential efficacy of novel therapeutic agents.

The aim of the current study was therefore to quantitatively characterize (using gadolinium) stroke-induced blood brain barrier disruption over time following transient middle cerebral artery occlusion in the rat. This is the model which has been used to assess the efficacy of Antibody A.

Induction of Cerebral Ischaemia

Transient (90 min) focal cerebral ischaemia was induced in 15 male Sprague Dawley rats, each weighing between 299±30 g. Under halothane anaesthesia, middle cerebral artery occlusion (MCAO) was carried out using the intraluminal thread technique as described previously (Enrique Zea Longa et al., "Reversible Middle Cerebral Artery Occlusion without Craniectomy in Rats", Stroke, Vol 20, No 1, January 1989, 84-91). Animals were maintained normothermic throughout the surgical procedure. Animals were maintained for 30 d at which time animals were killed by transcardial perfusion of ice cold 0.9% saline followed by 4% paraformaldehyde in 100 mM phosphate buffer.

Imaging Protocol

Animals were imaged at 8 time-points: baseline (pre-lesion) and at 1 h (n=6), 6 h (n=9), 12 h (n=6), 24 h (n=9), 7 d (n=11), 14 d (n=10) and 30 d (n=6) post-occlusion. At each time point, rats underwent T2 weighted scan for lesion delineation and region of interest (ROI) selection and 3×T1 weighted scans: 1 before and 2 after 0.5 ml/kg iv gadolinium-based contrast agent Magnevist (Gd-DTPA, Gadopentetate dimeglumine).

Behavioural Outcomes

Neurological score was conducted and body weight recorded every day for 7 d and then at 14 and 30 d post occlusion. Body Data are presented as mean±SEM.

Figure 3:
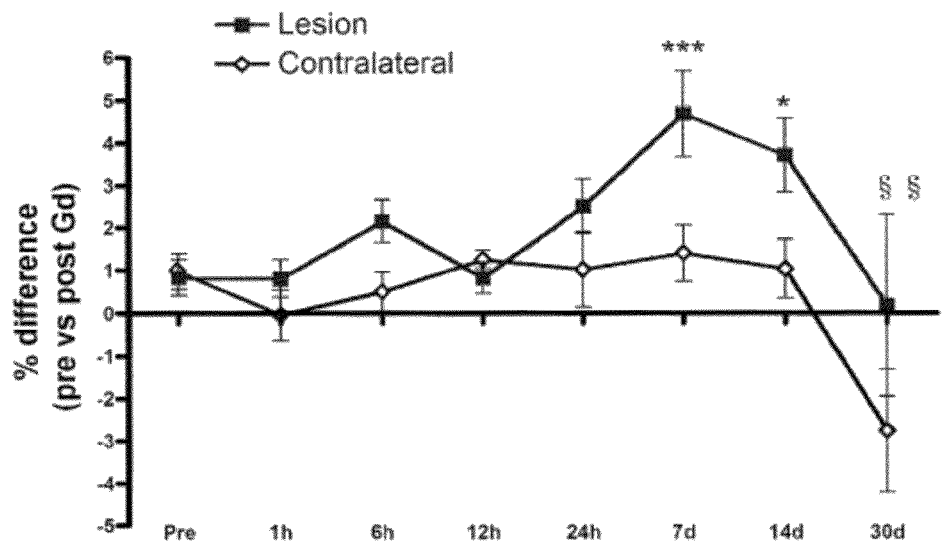
FIG. 3: Temporal assessment of BBB breakdown following transient MCAO in the rat.
Figure 2:
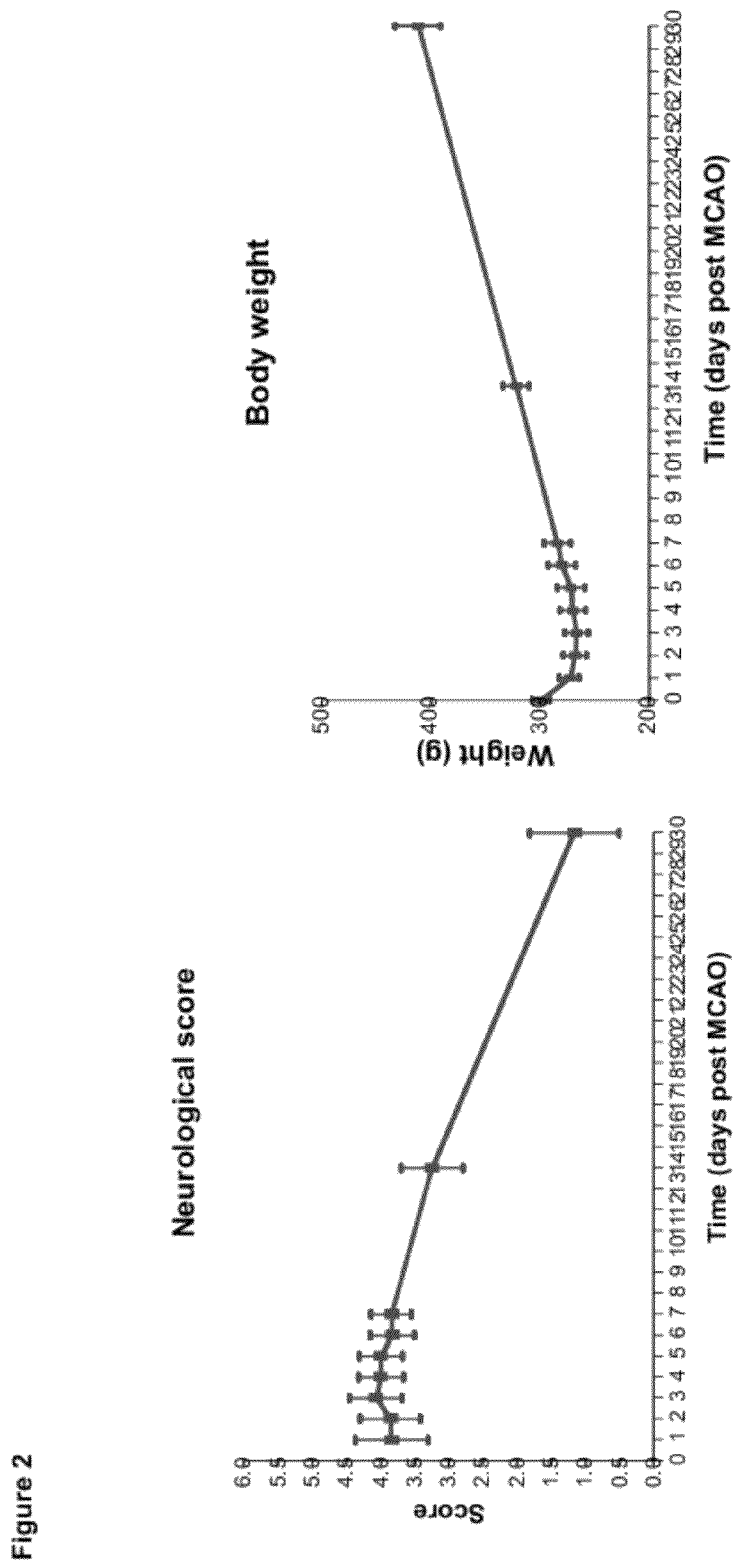
FIG. 2: Improvement in neuroscore and body weight gain following MCAO in the rat.
Figure 4:
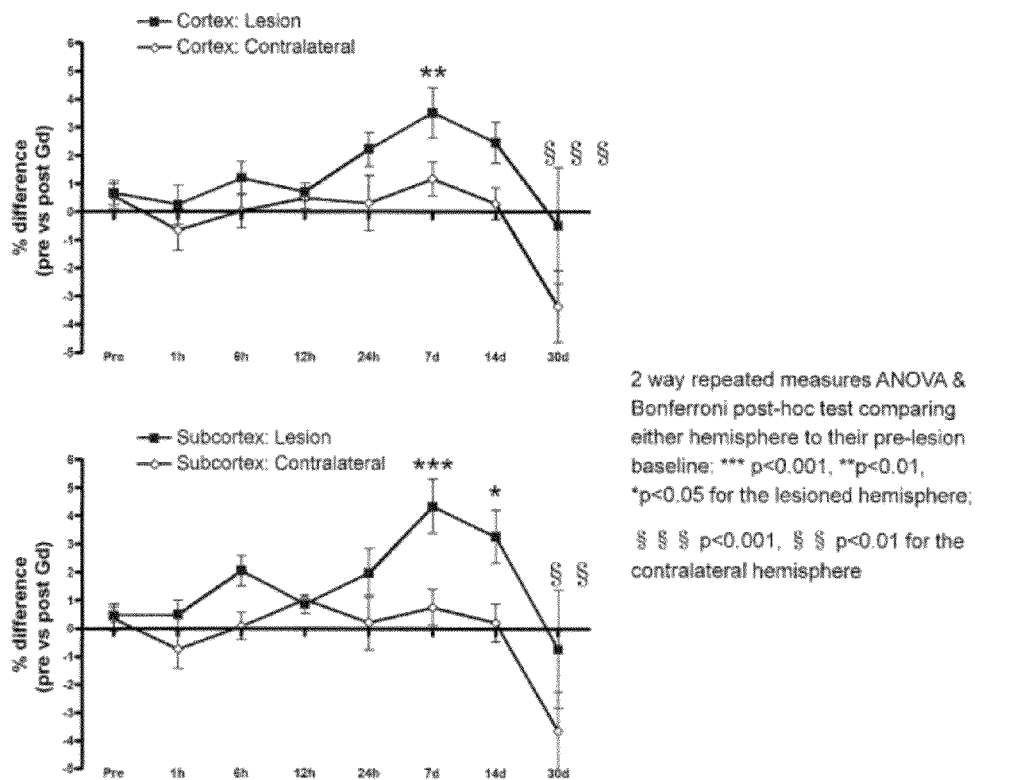
FIG. 4: Regional assessment of BBB breakdown following MCAO in the rat.

Results
Neurological Score & Body Weight
Following occlusion all animals demonstrated the expected neurological impairment which improved over time. This correlated well with an increase in body weight reflecting spontaneous recovery from stroke.
BBB Breakdown
Following transient MCAO, there was a significant decreased in neuroscore and body weight which improved over time (FIG. 2). In addition, there was a variable but non-significant increase in gadolinium signal up until 24 h post occlusion. This increase in signal reached maximal levels at 7 d and gradually decreased thereafter with significantly increased levels being detected at 7 d and 14 d post stroke (see FIG. 3). This increase in BBB permeability reflected increases at both the cortical and sub-cortical levels (FIG. 4).
Conclusions
Gd-DTPA is routinely used in clinical MR studies. Due to its size, Gd-DTPA is unable to cross the BBB until the BBB is disrupted. The data above demonstrates that while there is some leakage of the BBB early after injury (i.e. <24 h), it is only after 24 h that significant disruption to the BBB occurs in this model. This would suggest that in order to gain maximal CNS exposure, novel agents should be administered after 24 h but within 2 to 3 weeks following occlusion in this rodent model of stroke.

There are limited studies investigating BBB breakdown in human stroke, and it is unclear how this data may translate to man. In general, the assumption has been that the breakdown of the BBB is acute and therapies have the best chance of achieving efficacious exposure levels when administered as early as possible following injury. However this data does suggest that significant BBB damage may be delayed in subjects where transient occlusion or reperfusion occurs, and suggests that agents with low levels of CNS penetration may achieve higher levels of CNS exposure if administration is delayed beyond the 'acute' period.

Example 5

Figure 5:
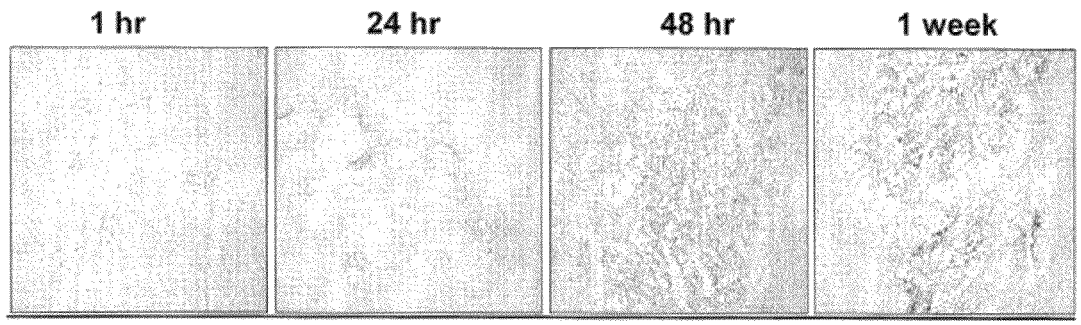
FIG. 5: Distribution of Antibody A in the ipsilateral (lesioned) hemisphere of rats administered with Antibody A, 1, 24, 48 h or 7 d following transient middle cerebral artery occlusion in the rat.

Administration of Anti-MAG Following Cerebral Ischemia: Evidence of Central Penetration Following Delayed Administration Introduction
The aim of these studies was to investigate the ability of the anti-MAG antibody Antibody A to enter the brain of rats and squirrel monkeys following focal cerebral ischemia.
Three independent studies have been conducted:
Study 1) Immunohistochemical assessment of Antibody A distribution when administered 1 h, 24 h, 48 h or 7 d following transient middle cerebral artery occlusion in the rat
Study 2) Immunohistochemical assessment of Antibody A distribution when administered 24 h following permanent ischaemia in the squirrel monkey
Study 3) Quantitative assessment of free Antibody A, and Antibody A co-localised with MAG when administered 24 h, 3 weeks and 6 weeks following transient middle cerebral artery occlusion in the rat
Study 1: Immunohistochemical Assessment of Antibody a Distribution when Administered 1 h, 24 h, 48 h or 7 d Following Transient Middle Cerebral Artery Occlusion in the Rat
Methods
Focal cerebral ischemia was induced in male Sprague Dawley rats (Charles River, UK) under isoflurane anaesthesia (in $O_2$: medical air 20:80) by occluding the right middle cerebral artery (MCA) for 90 minutes with intraluminal thread (silicone rubber coated 5.0 monofilaments, tip diameter 0.33±0.02 mm, from Doccol Corportation, USA) as previously described (David Virley et al., "A Temporal MRI Assessment of Neuropathology After Transient Middle Cerebral Artery Occlusion in the Rat: Correlations With Behavior", Journal of Cerebral Blood Flow & Metabolism, (2000) 20, 563-582). Following surgery, animals received Antibody A (10 mg/kg i.v.) or vehicle (i.v). Animals were divided into 8 groups (n=3) per group:
A=Dosed with Antibody A (10 mg/kg i.v.) at 1 h post occlusion
B=Dosed with vehicle at 1 h post occlusion
C=Dosed with Antibody A (10 mg/kg i.v.) at 24 h post occlusion
D=Dosed with vehicle at 24 h post occlusion
E=Dosed with Antibody A (10 mg/kg i.v.) at 48 h post occlusion
F=Dosed with vehicle at 48 h post occlusion
G=Dosed with Antibody A (10 mg/kg i.v.) at 7 d post occlusion
H=Dosed with vehicle at 7 d post occlusion
Six hours following dosing, animals were killed by transcardial perfusion of 0.9% saline followed by 4% paraformaldehyde in PBS and brains removed. Perfused-fixed brains were stored at +4° C. 4% paraformaldehyde in PBS for later processing by immunohistochemistry as described previously (Irving E. A. et al., "Assessment of white matter injury following prolonged focal cerebral ischaemia in the rat", Acta Neuropathol, (2001) 102, 627-635). Antibody A was detected using a donkey anti-human IgG (Jackson), followed by a rabbit anti-donkey IgG (Abcam,) and visualised using diaminobenzidine. Images were collected with an Olympus microscope using ANAlysis™ software.
Results
No immunoreactivity was detected in the ipsilateral (lesioned) or contralateral (non-lesioned) hemispheres of brains of vehicle treated animals. In those animals receiving Antibody A, no immunoreactivity was detected in tissue obtained from animals receiving Antibody A 1 h following MCA occlusion. In contrast, immunoreactivity was detected in the ipsilateral hemisphere of tissue taken from animals receiving Antibody A 24 h following MCA occlusion. Immunoreactivity was further increased in those tissue sections taken from those animals where dosing was delayed until 48 h and 1 week following occlusion (See FIG. 5).
Conclusions
The results from this study demonstrate that following i.v. dosing, Antibody A is able to penetrate into the lesioned (ipsilateral) hemisphere of rats following MCA occlusion. Maximal levels of Antibody A were detected when administration was delayed until 24 h and beyond which correlates well with the time-course of the breakdown of the blood brain barrier in this model as described in Example 4 above. This data supports the hypothesis that in order to achieve maximal exposure of Antibody A, administration should be delayed until 24 h following onset of ischaemia in this model. While it is unclear how this time course will translate to human stroke, this data does indicate that significant BBB damage may be delayed in subjects where reperfusion occurs, and suggests that agents with low levels of CNS penetration may achieve higher levels of CNS exposure if administration is delayed beyond the 'acute' period.
Study 2) Immunohistochemical Assessment of Antibody A Distribution when Administered 24 h Following Permanent Ischaemia in the Squirrel Monkey
According to the methods of Example 7, one animal underwent focal cortical infarct and Antibody A (30 mg/kg) was injected intravenously 24 h following the onset of ischemia and the animals sacrificed at 30 h post-infarct. Animals were perfuse fixed using 4% paraformaldehyde and brains processed for immunohistochemical assessment of Antibody A distribution as outlined in Example 5, study 1.

Results

Figure 6:
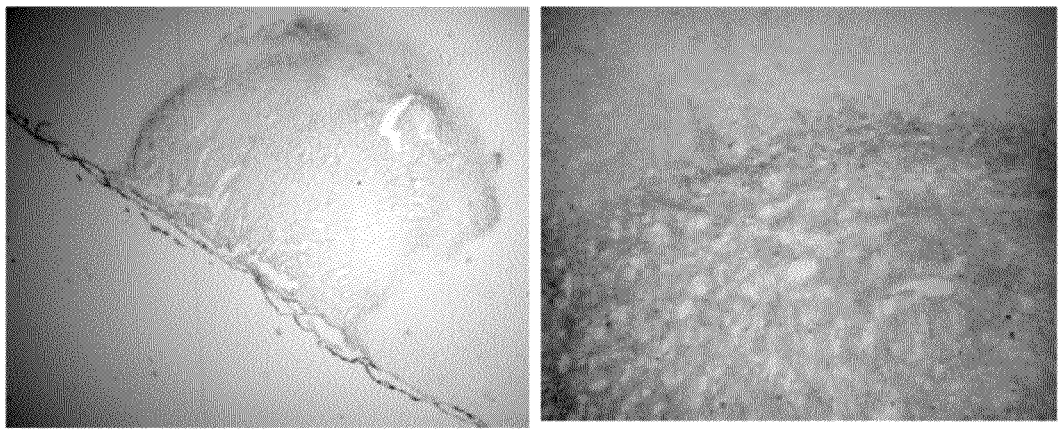
FIG. 6: Antibody A distribution within the lesion cortex (low magnification on left, higher magnification on right) when administered 24 h following permanent ischemia in the squirrel monkey.

Electrocoagulation resulted in a small focal cortical lesion. Antibody A was localised around the lesion site, with no immunoreactivity detected in intact tissue (FIG. 6).

Conclusion

This study confirms that Antibody A, when administered intravenously, is able to penetrate the lesioned brain of squirrel monkeys even when intravenous administration is delayed until 24 h post occlusion. This demonstrates that even when ischaemia is induced by permanent occlusion, Antibody A is still able to penetrate the brain even when administration is significantly delayed beyond the acute onset of injury. While the time-course of blood brain barrier disruption is unknown in this model, it does suggest that delaying administration is not detrimental to the ability of Antibody A accessing the lesioned area of the brain. Indeed, dosing Antibody A (10 mg/kg i.v.) 24 h following permanent occlusion in squirrel monkeys has been shown to improve behavioural outcome in this model (see Example 7). Since squirrel monkeys provide a translational step between rats and human, this data provides support that pharmacologically active exposure levels of Antibody A should be achievable in human stroke when dosed 24 h following focal ischemia, regardless of the presence or absence of reperfusion induced injury.

Study 3) Quantitative Assessment of Free Antibody A and Antibody A Co-Localised with MAG when Administered 24 h, 7 Days, 3 Weeks and 6 Weeks Following Transient Middle Cerebral Artery Occlusion in the Rat The aim of the current study was to extend the findings described above, and quantify the level of MAG, Antibody A and the combination of Antibody A co-localised with MAG in the rat following transient MCAO using laser scanning cytometry (LSC).

Part A: 3 Treatment Groups

Group 1 (n=14) received Antibody A (10 mg/kg i.v.) 24 h after MCAO, followed by weekly administrations of 6 more doses, Group 2 (n=19) received diluent i.v. 24 h after MCAO, then Antibody A (10 mg/kg i.v.) 7 days later, followed by 5 more weekly administrations of Antibody A Group 3 (n=17) vehicle rats received diluent 24 h after MCAO, followed by weekly administrations of 6 more doses.

Part B: 6 Treatment Groups, A-F.

Group A (n=7) received Antibody A (10 mg/kg i.v.) at 24 h after SHAM surgery, followed by 2 more doses at 7 and 14 days, killed 15 days after surgery Group B (n=6) received vehicle i.v. at 24 h after SHAM surgery, killed 48 hr after surgery Group C (n=5) received vehicle i.v. at 24 h after MCAO surgery, killed 48 hr after surgery Group D (n=10) received Antibody A (10 mg/kg i.v.) 24 h after MCAO surgery, followed by 2 more doses at 7 d and 14 d, killed 15 days after surgery Group E (n=10) received Antibody A (10 mg/kg i.v.) at 21 d after MCAO surgery, followed by 2 more doses at 28 and 35 days, killed 36 days after surgery Group F (n=11) received Antibody A (10 mg/kg i.v.) at 42 d after MCAO surgery, killed 43 days after surgery.

Methods

Transient cerebral ischemia was induced in male Sprague Dawley rats (Charles River, UK) under isoflurane anaesthesia (in $O_2$: medical air 20:80) by occluding the right middle cerebral artery (MCA) for 90 minutes with intraluminal thread (silicone rubber coated 5.0 monofilaments, tip diameter 0.33±0.02 mm, from Doccol Corportation, USA) as previously described (David Virley et al., "A Temporal MRI Assessment of Neuropathology After Transient Middle Cerebral Artery Occlusion in the Rat: Correlations With Behavior", *Journal of Cerebral Blood Flow & Metabolism*, (2000) 20, 563-582). Sham animals were treated exactly as MCAO animals, except that the thread was not pushed far enough to occlude the MCA but only to the bifurcation between internal carotid and pteregopalatine artery.

Animals from part A were killed by transcardial perfusion of 0.9% saline followed by 4% paraformaldehyde in PBS and brains removed. Perfused-fixed brains were stored at +4° C. 4% paraformaldehyde in PBS for later processing by immunohistochemistry as described above.

Animals from part B were killed by overdose of barbiturate anaesthesia, decapitated and a blood sample was taken from the trunk. Brains were removed immediately and frozen on chilled isopentane (approximately −40° C.). Within 2 h from the removal, the brains were removed and stored at −80° C.

IHC Method

Frozen sections were cut at 5 microns using the cryojane tape transfer system. Sections were dried overnight then either placed in buffer (4% paraformaldehyde perfused brains) or fixed in 4% paraformaldehyde for 10 minutes (fresh frozen). Immunohistochemistry was carried out using the Leica Bond Max. Sections were incubated for 10 minutes with BioFX dual endogenous enzyme block followed by 30 minutes with Biocare Med Rodent Block R. Mouse anti-human IgG (Invitrogen #05-4200) was diluted 1:50 and incubated on the sections for 30 minutes followed by 30 minute incubation with Biocare Med mouse on rat HRP (horse radish peroxidise) polymer detection. Leica DAB refine was added for 10 minutes followed by a 5 minute incubation with Leica DAB enhancer.

For dual IHC staining, goat anti-rat MAG (R&D systems #AF538) was diluted 1:100 and added to sections for 60 minutes. This was followed by a 30 minute incubation with Biocare Med biotinylated mouse anti-goat IgG. Subsequently, Biocare Med Streptavidin alkaline phosphatase was added for 30 minutes, followed by Leica Refine red chromagen for 20 minutes then Leica hematoxylin for 5 minutes.

Laser Scanning Cytometry Method

IHC labeled brain sections were loaded on the iCyte® Laser Scanning Cytometer. A mosaic scan of the entire brain section was performed using a 20× objective with a 20 µm step size. A second, high resolution scan was performed using the 20× objective with a 0.5 µm step size to quantify MAG and Antibody A. Phantom contours were applied (2500 per scan field) and the long red fluorescence intensity of MAG was collected and plotted against the 488 laser line absorbance of Antibody A. Gated regions were created on a scatter plot of MAG maximum pixel intensity vs. Antibody A maximum pixel intensity as follows:

R1=no signal or background levels falling below detector threshold;
R2=Antibody A only;
R3=Antibody A co-localised with MAG; and
R4=MAG only.

The sum of the expression values of gated regions (R2, R3 and R4) for each sample was collected.

Statistical Analysis

Analysis of variance was performed using log 10 transformed data, not compensated for spillover signal. Means and 95% confidence intervals were predicted from the anova model, and back transformed to provide geometric means with confidence intervals. Differences from vehicle control (with 95% confidence intervals) were estimated on the log 10 scale using the anova model. These differences on the log scale were back transformed to provide ratios to the vehicle control, with confidence intervals. P values are provided for each comparison (labelled 'Raw p'). To protect against false positive risk due to multiple comparisons, adjusted p values from the Benjamini-Hochberg method are also shown which control the false discovery rate.

Results

Quantification of the staining for MAG, Antibody A and Antibody A co-localised with MAG was carried out for all animals completing the study.

Figure 7:
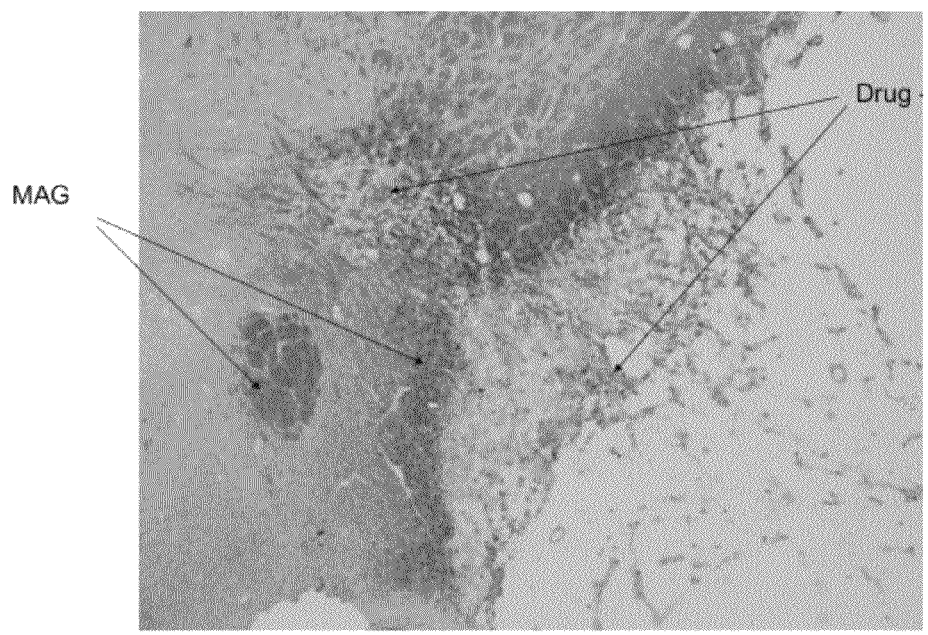
FIG. 7: Visualisation of the staining for MAG, Antibody A and Antibody A co-localized with MAG following MCA occlusion (lesioned hemisphere) from Example 5, study 3, part A.
Figure 8:
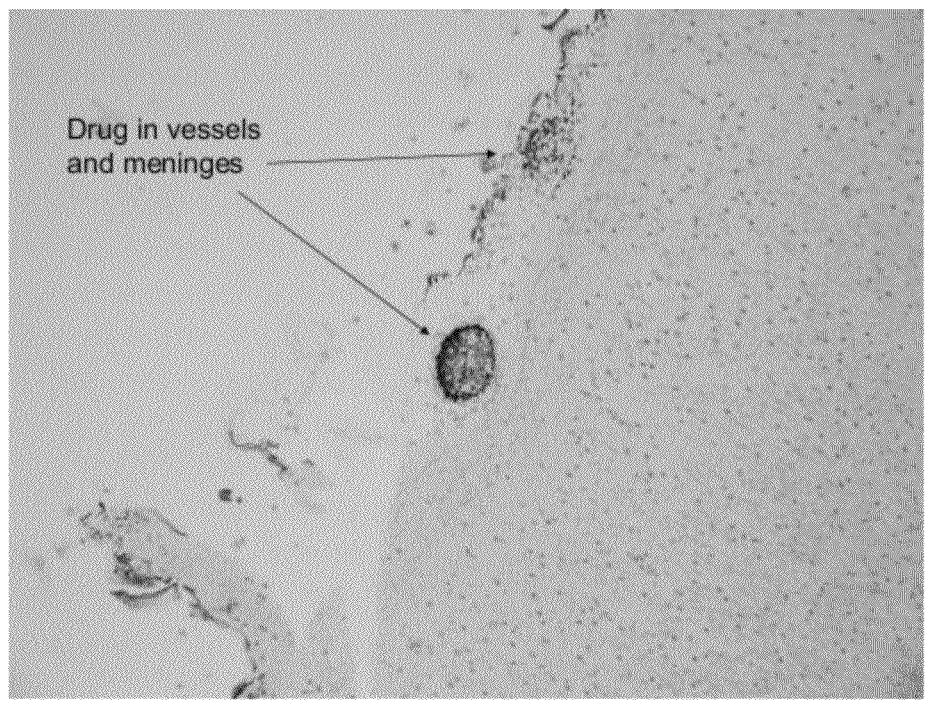
FIG. 8: Visualisation of the staining for MAG, Antibody A and Antibody A co-localized with MAG following MCA occlusion (non-lesioned hemisphere) from Example 5, study 3, part A.
Figure 9:
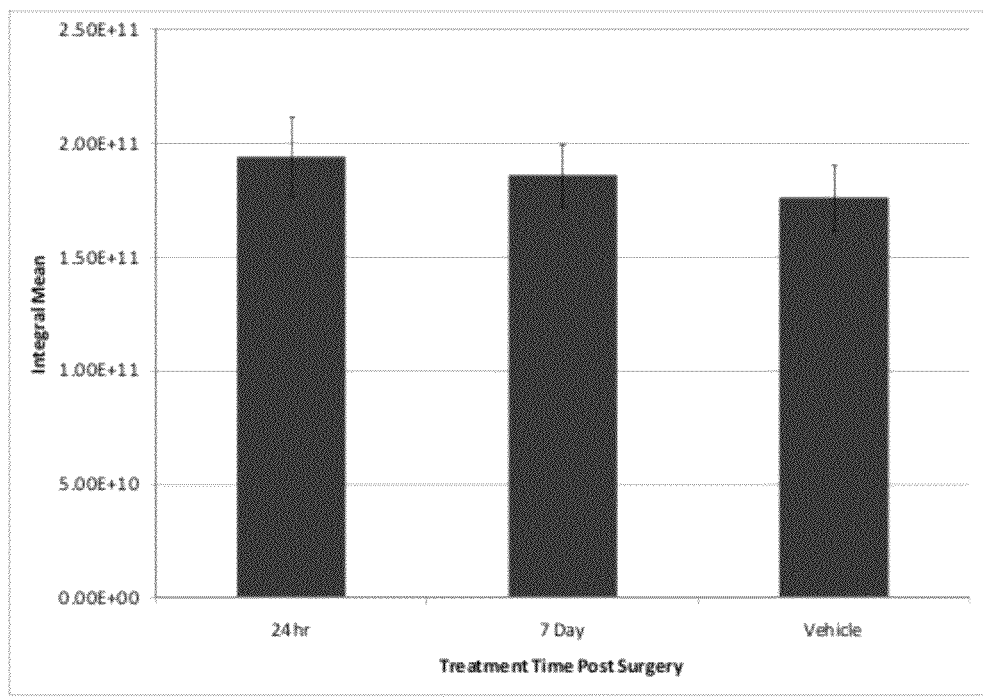
FIG. 9: Quantification of staining for MAG alone from Example 5, study 3, part A.
Figure 10A:
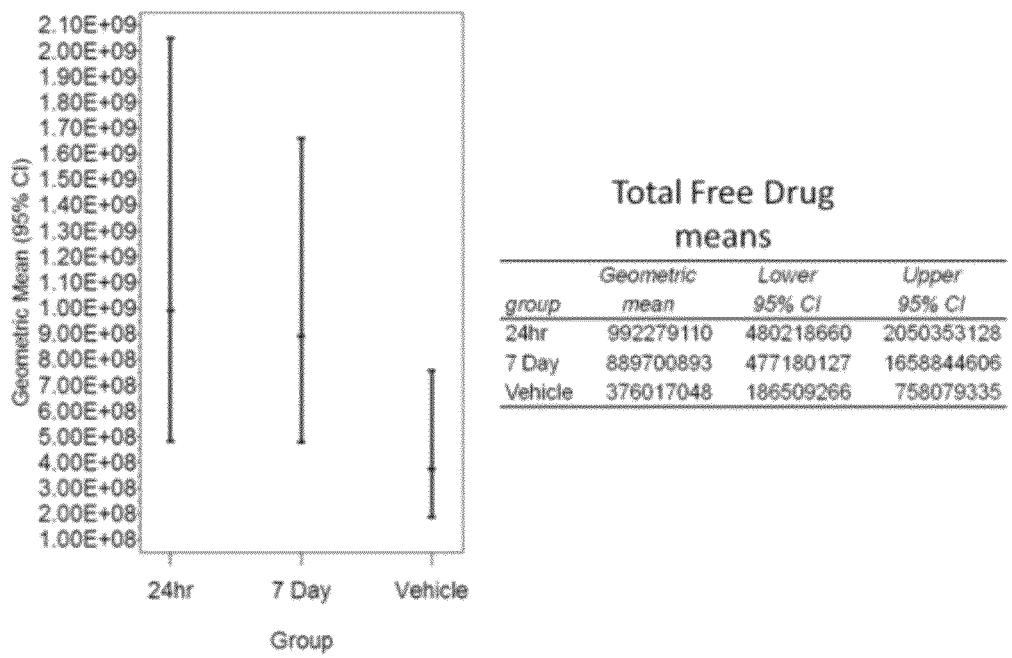
FIG. 10A: Free drug expression after Antibody A treatment at 24 hours and 7 days following MCAO in rats from Example 5, study 3, part A. Results show geometric mean (95% confidence intervals).
Figure 10B:
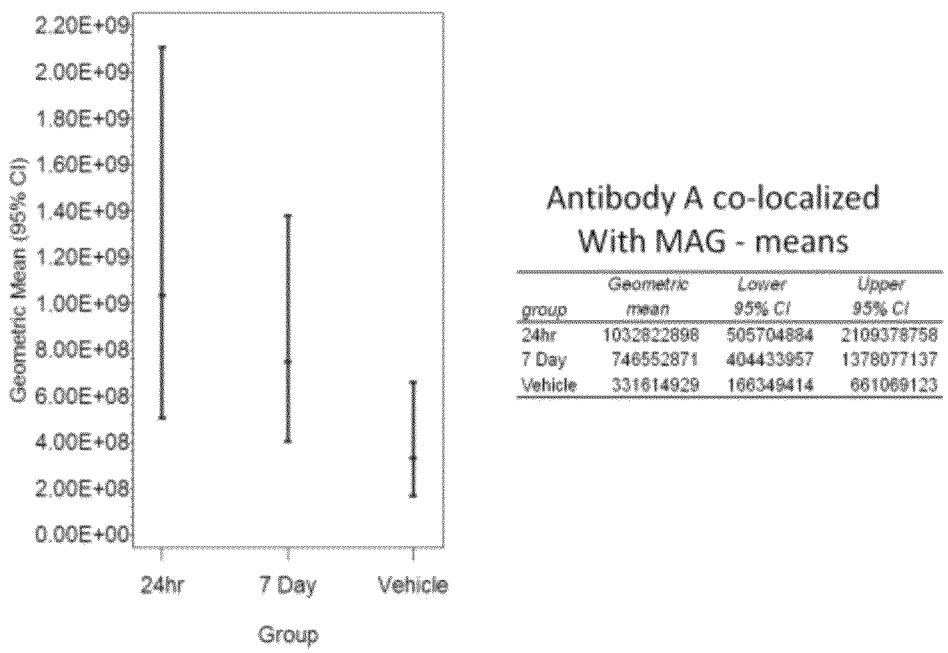
FIG. 10B: Co-localised drug expression after Antibody A treatment at 24 hours and 7 days following MCAO in rats from Example 5, study 3, part A.

In part A, as a result of the MCAO surgery the level of MAG increased and staining was predominantly localized in the penumbra, therefore this was also the area of highest co-localisation with Antibody A (FIG. 7). On the contralateral hemisphere (non-lesioned), there was no staining of MAG and staining of the drug was limited to blood vessels and meninges (FIG. 8). Staining for MAG alone was consistent in all treatment groups as expected since all 3 groups underwent MCAO (FIG. 9). Only background staining of free Antibody A or Antibody A co-localised with MAG was detected in vehicle treated animals as expected. There was borderline evidence of an increase over vehicle for free drug at both 24 hours (p=0.0710) and at 7 days (p=0.0710) (FIG. 10A) but not sufficient evidence to be statistically significant. For antibody A co-localised with MAG, there was borderline evidence of an increase over vehicle at both 24 hours and 7 days. However, at 24 hours the difference was very close to significance (p=0.0517) (FIG. 10B).

Figure 11A:
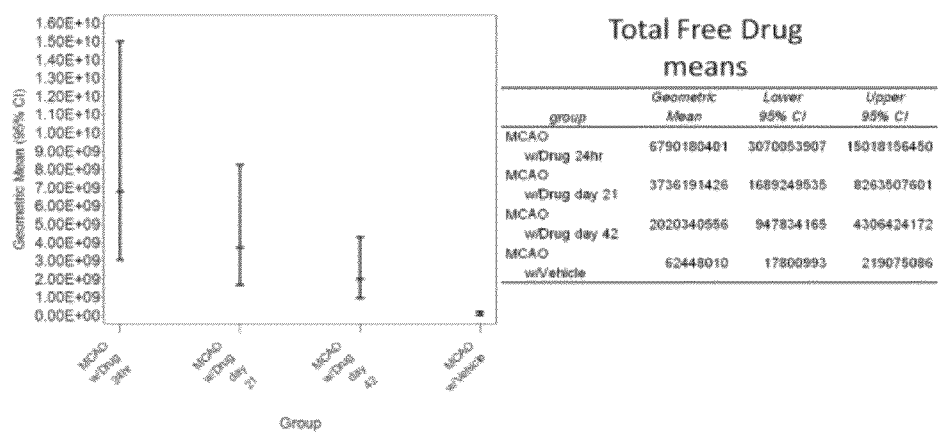
FIGS. 11A & 11B: Free and co-localised drug expression after Antibody A treatment at 24 hours, 21 days and 42 days following MCAO in rats from Example 5, study 3, part B.
Figure 11B:
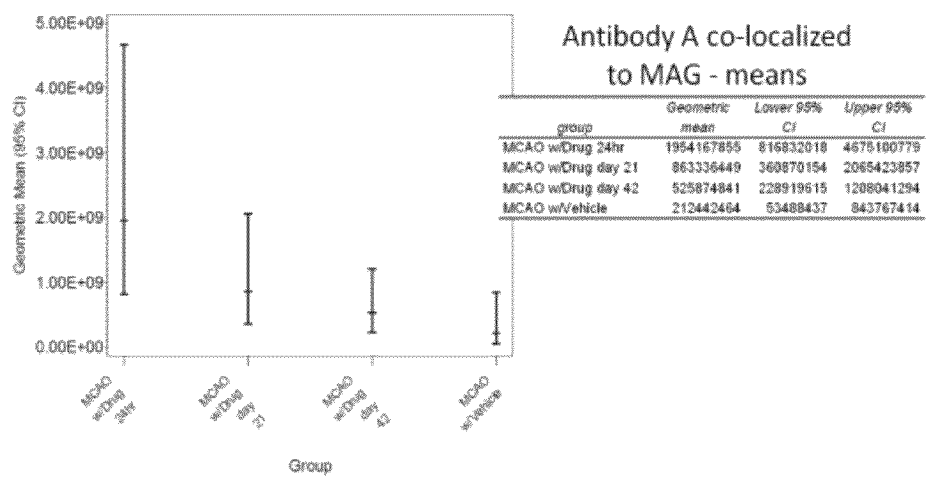

In part B, one animal was removed from the analysis, since it showed vastly increased quantification levels of both free Antibody A and Antibody A co-localised to MAG which skewed the results significantly in the 24 hour treatment group. This animal had a much larger lesion involving almost the whole hemisphere, and was considered to be an outlier, hence was excluded. The sham animals treated with Antibody A showed the lowest level of free Antibody A, possibly indicating the fact that the blood brain barrier in these animals is still intact. Sham animals treated with vehicle, and MCAO animals treated with vehicle, showed only background levels of Antibody A and Antibody A co-localised with MAG as expected. There was significant evidence of a difference (p<0.01) in free drug between MCAO drug treated rats and MCAO vehicle treated rats at 24 hours, 21 days and 42 days (FIG. 11A). For co-localised drug there was borderline evidence of a difference from vehicle at 24 hours (p=0.054) in the MCAO rats and this effect progressively diminished at 21 days and 42 days (FIG. 11B).

Conclusions

MAG expression was observed in all MCAO rats and MAG images clearly showed co-localisation of MAG with Antibody A around the lesion penumbra confirming that Antibody A can access the areas where MAG expression is present following an infarct, even when administration is delayed beyond 24 hours following the onset of ischemia.

Statistical analysis confirmed that there was significant evidence of higher levels of free drug in the Antibody A treated MCAO rats compared with vehicle when treated at all timepoints in part B (24 hours, 21 days, 42 days), although part A showed only borderline evidence of significance at 7 days treatment and not 24 hours suggesting disruption of the blood brain barrier occurs robustly only after 24 hours, but remains compromised for up to 42 days. There was borderline evidence of higher expression of co-localised drug in Antibody A treated MCAO rats treated at 24 hours compared to vehicle treated in both studies and this difference diminished at later timepoints (7 days, 21 days, 42 days) suggesting early treatment may be optimal for target engagement with the drug.

Example 6

Administration of Anti-MAG Antibody to Rats: Timing of First Dose 24 h Vs 7 d

Introduction

Together, the data outlined in Examples 4 and 5 indicate that optimal exposure of Antibody A should be obtained when administered from 24 h following MCA occlusion in the rat. Furthermore, data presented in Examples 2 and 5 indicates that MAG expression increases gradually following the onset of ischemia, with levels remaining elevated for several weeks. This suggests that the optimal dosing regimen for Antibody A would involve delayed administration with a dosing paradigm that will maintain efficacious exposure levels for the duration of elevated MAG expression. The aim of the present study was therefore to investigate the ability of Antibody A to improve functional recovery, following transient MCA occlusion in the rat when administered weekly from 24 h or 7 d following occlusion.

Methods

Transient cerebral ischaemia was induced in 66 male Sprague Dawley rats (Charles River, UK; mean±sd weight 361±21 g) under isoflurane anaesthesia (in $O_2$: medical air 20:80) by occluding the right middle cerebral artery (MCA) for 90 minutes with intraluminal thread (silicone rubber coated 5.0 monofilaments, tip diameter 0.33±0.02 mm, from Doccol Corporation, USA) as previously described (David Virley et al., "A Temporal MRI Assessment of Neuropathology After Transient Middle Cerebral Artery Occlusion in the Rat: Correlations With Behavior", *Journal of Cerebral Blood Flow & Metabolism*, (2000) 20, 563-582).

A total of 16 rats were excluded from the study because of sub-arachnoid haemorrhage (confirmed by MRI at 24 h post surgery, n=8), or because they died overnight (n=3) or were euthanised the day after surgery (n=3) or at a later date (n=2) due to excessively severe symptoms, as required by the Home Office Project Licence.

Following confirmation of successful occlusion (assessed by tight circling), animals were randomised to the following treatment groups:

Group 1 (n=14): received Antibody A (10 mg/kg i.v) 24 h after MCAO, followed by weekly administrations of 6 more doses of Antibody A (10 mg/kg i.v.)

Group 2 (n=19): received diluent (1 mL/kg i.v.) 24 h after MCAO, then Antibody A (10 mg/kg i.v.) 7 days later, followed by 5 more weekly administrations of Antibody A (10 mg/kg i.v.)

Group 3 (n=17): received diluent (1 mL/kg i.v.) 24 h after MCAO, followed by weekly administrations of 6 more doses Behavioural Assessments Functional recovery was assessed using a number of tests:

Neurological Scoring

A neurological assessment involving an 18 point score, modified from A. J. Hunter, et al., "Functional assessments in mice and rats after focal stroke", Neuropharmacology, 39 (2000), 806-816 and M. Modo et al., "Neurological sequelae and long-term behavioural assessment of rats with transient middle cerebral artery occlusion", Journal of Neuroscience Methods, 194 (2000), 99-109, was used. This comprised a battery of 9 tests that include assessment of spontaneous motility, grooming, righting reflex, ability to grip a horizontal bar, visual paw placement, spontaneous and induced (tail lift) circling, forelimb flexion and contralateral reflex (lateral push). The maximum score that the healthy rat can achieve is 18. Scoring was performed once before surgery and daily for the first 7 days after MCAO, then once per week throughout the study.

Staircase Test

The staircase test, originally developed by C. P. Montoya, et al., "The "staircase test" a measure of independent forelimb reaching and grasping abilities in rats", Journal of Neuroscience Methods, 36 (1991), 219-228, was performed as described by David Virley, et al., "A Temporal MRI Assessment of Neuropathology After Transient Middle Cerebral Artery Occlusion in the Rat: Correlations With Behavior", *Journal of Cerebral Blood Flow & Metabolism*, (2000) 20, 563-582. Staircase testing equipment was purchased from Campden Instruments Ltd. Coco-pops (Tesco) were used as food bait. Animals were trained each weekday for 3-4 weeks before surgery until they satisfied inclusion criteria of retrieval of at least 2 coco-pops, and displacement of less than 7 coco-pops, per side per day for 3 consecutive days. Performance was scored as the number of coco-pops recovered and/or displaced from each side. Each data point represents the mean of two trials per day over three days of testing per time-point. The last three training days pre-surgery, after the animal has satisfied inclusion criterion, were used as baseline score. Animals were tested again 2, 4 and 6 weeks after MCAO. Before each test session, the rats were placed on a mild food restriction diet comprising of 15 g food pellets per rat (previously determined to be needed to maintain rats at 80-85% of free feeding weight).

Bilateral Asymmetry (Sticky Tape) Test

Bilateral asymmetry test probes sensorimotor neglect as described previously (M. Modo, et al., "Neurological sequelae and long-term behavioural assessment of rats with transient middle cerebral artery occlusion", Journal of Neuroscience Methods, 194 (2000), 99-109; Timothy Schallert, et al., "CNS plasticity and assessment of forelimb sensorimotor outcome in unilateral rat models of stroke, cortical ablation, parkinsonism and spinal cord injury", Neuropharmacology, 39 (2000), 777-787). For this test, a 1 cm-wide strip of sticky tape (Micropore, 3M) was firmly wrapped around each forepaw and the latency to remove the tape was recorded in two trials per test point, each trial lasting up to three minutes. Each data point represents a mean of two trials. Prior to MCAO surgery, animals were trained in 4 such sessions; the fifth session (1-3 days before MCAO) was treated as a baseline measure after which the animals were repeatedly tested at 1, 3, 5 and 7 weeks post-MCAO.

Cylinder Test

Cylinder test measures forelimb-use asymmetry and limb use during exploratory behaviour (Timothy Schallert, et al., "CNS plasticity and assessment of forelimb sensorimotor outcome in unilateral rat models of stroke, cortical ablation, parkinsonism and spinal cord injury", Neuropharmacology, 39 (2000), 777-787). The rats were placed inside a glass beaker (28.5 cm height and 13 cm base diameter) for up to 3 minutes and the number of contacts between the glass wall and each forepaw was counted. Each test point comprised of two such trials and each data point represents a mean of the two trials. Rats were tested at 1, 3, 5 and 7 weeks post-MCAO.

Magnetic Resonance Imaging

Each rat underwent two MR imaging sessions in order to visualize stroke lesion at an early acute time-point, 24±2 h after MCAO, and a later chronic time-point at 46 days after MCAO. MR imaging was T2-weighted using fast spin echo with TR=4 s, effective TE=60 ms, 45×0.6 mm thick slices and 0.31×0.31 mm in plane resolution.

Collection of Tissue and Blood

Animals were killed by transcardial perfusion of 0.9% saline followed by 4% paraformaldehyde in PBS and brains removed. Prior to the start of perfusion, a terminal blood sample was withdrawn from the heart, part of which was centrifuged to separate plasma from blood cells, generating total of 2 mL of whole blood and 1 mL plasma per rat. The samples were thereafter stored at −80° C. Perfused-fixed brains were stored at +4° C. 4% paraformaldehyde in PBS for later processing by immunohistochemistry.

Data Analysis

MRI Data

Raw data were transformed using in house software and converted to Analyze format. Brains were masked using rbet software (D. Lythgoe, Institute of Psychiatry) to exclude all non-brain voxels. The masked brains images were then spatially normalized to a standard template using a 12-parameter affine co-registration algorithm (SPM'99). Lesion volumes were measured using DispImage software (D. Plummer, UCL) by contouring (or manually delineating in a few cases) the lesion outline that remained after images were thresholded above 2 SDs of the MR signal intensity in the unaffected contralateral hemisphere. Brain volumes were obtained by automatic contouring. Differences in lesion and brain volumes over time and between groups were analyzed by repeated measures ANOVA using Prism 4 for Macintosh (GraphPad) software.

Statistical Analysis

Prism 4 for Macintosh (GraphPad) performed all statistical data analysis using repeated measures or one-way ANOVA with Bonferroni post-hoc tests to determine differences between experimental groups and time-points. $p<0.05$ was considered significant throughout. All graphical data are shown as mean±sem unless otherwise stated.

Results

Figure 12:
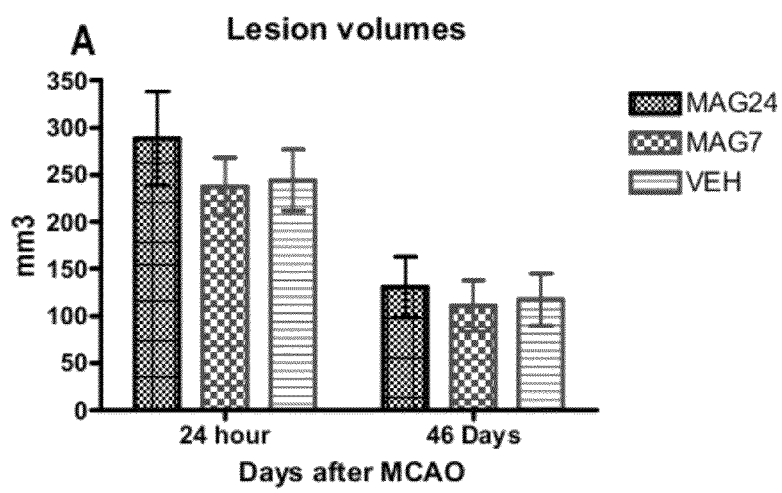
FIG. 12: Lesion volumes at 24 h and 46 d following transient MCAO in the rat. Data presented as Mean±SEM.

There were no significant differences detected in lesion or brain size between the treatment groups in either cohort (FIG. 12), demonstrating that Antibody A had no neuroprotective properties when administered 24 h or 7 d following MCAO.

Weight in animals steadily increased over time, but there were no significant differences between the treatment groups in either absolute weight or weight minus baseline (pre-operative) weight.

Neurological score decreased after MCAO surgery (lowest mean score was 10.7±0.5 at day 1 after MCAO), then increased to almost baseline over time, but there were no significant differences between the treatment groups.

Further statistical analysis supplied by GSK noted an improvement in neurological scores of the cohort treated with Antibody A at 24 h, at weeks 2 and 4 post-MCAO. This was not lesion type dependent.

Figure 13:
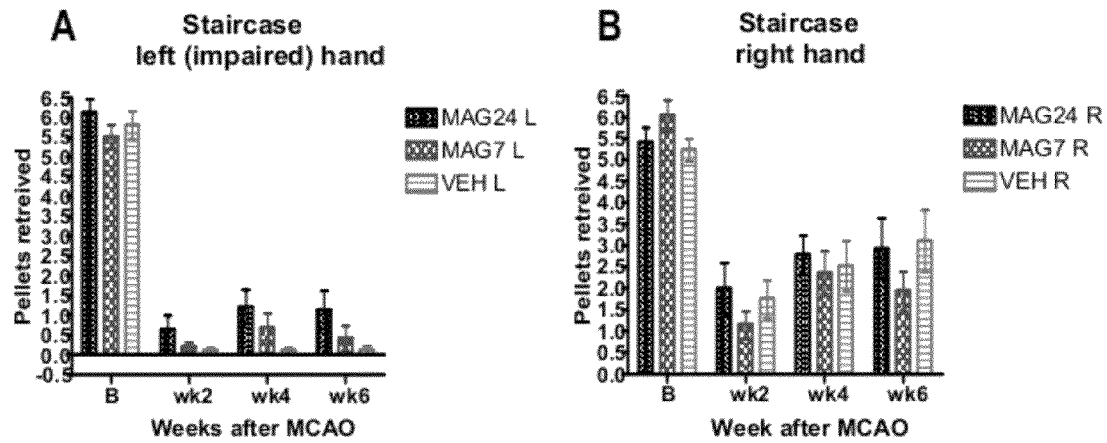
FIG. 13: Treatment with Antibody A 24 h and 7 d following MCAO significantly improved performance in the staircase test. Data presented as Mean±SEM.

The Staircase test involves the skilled use of forelimb, but is also dependant on hind-limb function with respect to balance and ability to navigate the staircase apparatus. In contrast to other tests used in this study, it is also motivationally-directed (animals are food deprived). As expected, all animals demonstrated a significant impairment after MCAO on both sides 2 weeks following MCAO, although the deficit was greater on the affected side (that is contralateral to the lesion, left hand side) (FIG. 13). The ability of the animals to retrieve pellets from the staircase with their right paw recovered at a similar rate in both Antibody A and vehicle treated animals. In contrast, retrieval of pellets by the left hand was enhanced in those animals receiving Antibody A starting 24 h or 7 d following MCAO (FIG. 13). The degree of recovery observed was greater in the group that received Antibody A starting 24 h following MCAO.

The functional recovery offered by Antibody A in the staircase task was not found in the cylinder or sticky label test. In these tasks, vehicle and Antibody A treated animal recovered at the same rates. The reasons for this are not clear, however it is possible that due to the predominance of these tasks on forelimb function may explain the lack of effect. In general terms, hindlimb function is regained more quickly than forelimb function in rats following MCAO. The hindlimb cortex resides closer to the penumbra of the lesion in this model than the forelimb cortex. Since MAG expression is markedly increased in the penumbral regions, it is possible that recovery offered by Antibody A may be limited to functions dependant on these specific brain regions.

The deficits detected in the cylinder test are known to be driven by caudate damage. In this model caudate damage is at the core of the lesion and therefore in the absence of significant neuroprotection in this area of the brain it is not surprising that no improvement in function was detected.

Conclusion

The results of the current study demonstrate that Antibody A can promote functional recovery in the rat following transient MCAO, even when administration is delayed up to 7 d following MCAO. However the enhanced recovery was more robust when administration was initiated 24 h following MCAO. This confirms that efficacious CNS exposure levels can be obtained even when administration of Antibody A was delayed beyond the acute phase. This supports the rationale for similar delay to dosing in human stroke.

Example 7

Correlation of Rat Dosing to Higher Species:
Squirrel Monkey

Introduction

The stroke field is littered with examples of where positive efficacy, as determined using rodent models of stroke, has failed to translate into clinical efficacy. It is therefore recommended that efficacy should be demonstrated in a non-human primate model prior to progression to human stroke (STAIR, Stroke, 1999, 30:2752-2758) to increase confidence in the likelihood that efficacy will translate forward to the clinic. The primary goal of this study was therefore to evaluate the ability of Antibody A to enhance motor behavioural recovery in a non-human primate model of cortical ischemia. Additional assessments (neurophysiological function and neuroanatomical connections) were utilised to further understand the mechanism underlying functional recovery.

Methods

A total of 9 squirrel monkeys were assigned to one of two groups, differing only with regard to whether they received post-infarct injections of Antibody A (30 mg/kg i.v.) or vehicle (acetate buffer). Injections were made at 24 hrs post-infarct and weekly thereafter for six weeks (i.e. d1, d8, d15, etc.). Immediately preceding weekly drug/vehicle injections, a blood sample was collected for analysis of plasma levels of circulating anti-MAG. The first post-infarct behavioural testing (probe trials) was conducted on day 3 post-infarct, then weekly on the day after injection (i.e., d9, d16, etc.) for six weeks. No specific rehabilitative procedures were employed, thus reflecting a "spontaneous" recovery condition (the "S" abbreviation in the group designations). Behavioural testing was filmed for later analysis and performance scores were compared between groups to assess behavioural recovery associated with each experimental condition.

At seven weeks post-infarct, all monkeys underwent a second surgical procedure, during which motor representations in M1 (primary motor cortex) and PMV (ventral premotor cortex) were remapped to assess neurophysiological reorganization associated with each experimental condition. At the conclusion of the second mapping experiment, a neuronal tract tracer, biotinylated dextran amine (BDA), was injected into the centre of the PMv hand representation. After 12 days (tracer uptake and transport time), monkeys were euthanized and the cortical tissue harvested for histological processing.

Surgical Procedures

Monkeys were pre-anesthetized with ketamine (20 mg i.m.), the trachea intubated, the saphenous vein catheterized, and the monkey placed into a stereotaxic frame. Then, under aseptic conditions and halothane-nitrous oxide anesthesia, a craniectomy (~1.5 cm square) was performed over primary motor and premotor cortex contralateral to the monkey's preferred hand, and the dura was excised. Inhalation anesthesia was withdrawn, and ketamine, supplemented by diazepam, was administered intravenously. Vital signs (heart rate, oxygen saturation, respiration rate, expired carbon dioxide, core body temperature, infusion rate of dextrose/Ringers fluid solution) was monitored throughout the experiment and maintained within normal limits (R J Nudo, et al., (2003) "A squirrel monkey model of poststroke motor recovery", ILAR J., 44:161-174). Following a neurophysiological mapping procedure (see below), inhalation anesthesia was reinstated, the dura replaced by silicone film, the bone flap cemented into place with dental acrylic, and the incision sutured and treated with local anesthetic and antibiotics. Monkeys were monitored until alert, then returned to their home cages. See Nudo R. J. and Milliken G. W., "Reorganization of movement representations in primary motor cortex following focal ischemic infarcts in adult squirrel monkeys", Journal of Neurophysiology, 1996, 75:5, 2144-2149 and Plautz E J, et al., "Effects of Repetitive Motor Training on Movement Representations in Adult Squirrel Monkeys: Role of Use versus Learning", Neurobiology of Learning and Memory, 74, 27-55 (2000).

Cortical Mapping Procedures

Established neurophysiological mapping techniques (intracortical microstimulation, ICMS) were used to derive detailed maps of movement representations in the distal and proximal forelimb areas of primary motor (M1) and ventral premotor (PMv) cortex contralateral to the monkey's preferred hand (H J Gould 3$^{rd}$ et al., (1986) "The relationship of corpus callosum connections to electrical stimulation maps of motor, supplementary motor, and the frontal eye fields in owl monkeys", Journal of Comparative Neurology, 247:297-325; R. J. Nudo, et al., "Neurophysiological Correlates of Hand Preference in Primary Motor Cortex of Adult Squirrel Monkeys", The Journal of Neuroscience, August 1992, f(8): 2918-2947; Plautz E J, et al., "Effects of Repetitive Motor Training on Movement Representations in Adult Squirrel Monkeys: Role of Use versus Learning", Neurobiology of Learning and Memory, 74, 27-55 (2000). Briefly, a microelectrode (tapered and bevelled glass micropipette, 10-25 µm o.d. tip, filled with 3.5M saline) was introduced into cortical layer V on a grid pattern (350-500 µm interpenetration distances) with reference to surface vasculature. At each site, intracortical microstimulation (ICMS) was used to determine the movement(s) evoked at threshold current levels (restricted to ≤530 µA to limit current spread). Pulse trains (thirteen 200-µsec pulses at 350 Hz) were repeated at 1 Hz, and evoked movements were described using conventional terminology. Mapping proceeded until the distal forelimb (or hand) representation, composed of finger, thumb, wrist, and forearm movements, was fully surrounded by proximal (e.g. elbow, shoulder, trunk, face) representations or by non-responsive sites. A computer algorithm was used to unambiguously delineate functional boundaries for analysis of representational areas (R. J. Nudo, et al., "Neurophysiological Correlates of Hand Preference in Primary Motor Cortex of Adult Squirrel Monkeys", The Journal of Neuroscience, August 1992, f(8): 2918-2947). A total of two ICMS mapping procedures were performed: the first, after pre-infarct training and baseline testing was completed; the second, seven weeks after the infarct was created and experimental treatments were completed.

Cortical Infarct Procedure

Based on ICMS mapping, the surface vasculature overlying a selected region of the M1 hand representation was occluded by bipolar electrocoagulation to create the ischemic injury (W M Jenkins and M M Merzenich (1987), "Reorganization of neocortical representations after brain injury: a neurophysiological model of the bases of recovery from stroke", Progress in Brain Research, 71:249-66; Nudo R. J. and Milliken G. W., "Reorganization of movement representations in primary motor cortex following focal ischemic infarcts in adult squirrel monkeys", Journal of Neurophysiology, 1996, 75:5, 2144-2149). The infarct targeted approximately 80% of the M1 hand representation while sparing as much of the surrounding proximal representation as possible. Guided by vasculature constraints, the infarct target was principally in the caudal portion of the M1 hand area, intentionally sparing hand representations in the rostral portion of the map. Coagulated vessels included fine arterial and venous capillaries as well as larger vessels but avoided pass-through arteries supplying other cortical areas. Although this technique does not mimic clinical stroke per se, it is advantageous in that it produces a very selective focal ischemic injury with sharp borders. The infarct was created at the conclusion of the first cortical mapping procedure, after inhalation anesthesia had been reinstated. Occluded vessels were monitored for several minutes for evidence of reperfusion and re-occluded as needed. A digital image of the infarct was acquired to compare to the intended target and to delineate borders during map analysis.

Behavioural Testing

All behavioural testing/training was conducted on a modified Klüver board apparatus. This device consists of a Plexiglas board with five food wells of 5 mm depth and varying diameters (25 mm to 9.5 mm diameter; termed wells 1-5 respectively) drilled into its surface. The board is attached to the front of the monkey's home cage, and requires minimal adaptation time until animals are performing the task. The motor task consists of reaching through the cage bars, inserting one or more fingers into a well, and retrieving a small food pellet (45 mg) that are placed one at a time into one of the five food wells. All task performance sessions were videotaped for later analysis. Measures of motor performance included number of finger flexions required to retrieve a pellet (flexions/retrieval), retrieval success rate, time required to perform retrievals, and the rate of aiming errors during reaching (Nudo R. J. and Milliken G. W., "Reorganization of movement representations in primary motor cortex following focal ischemic infarcts in adult squirrel monkeys", Journal of Neurophysiology, 1996, 75:5, 2144-2149).

Results

Nine monkeys, identified as GSK1-GSK9, were used in the efficacy study, but only seven monkeys completed the study. Two monkeys, GSK2 and GSK6, died during the experimental period. Neither death was attributable to the use of Antibody A. GSK2 died approximately two weeks after the infarct surgery. Necropsy report revealed no proximate cause of death, although it noted moderate intestinal abnormalities (enteritis) and a mild respiratory abnormality (pneumonitis). GSK2 had received two injections (24 hrs and 1 wk post-infarct) of vehicle solution prior to death. GSK6 died of acute respiratory and cardiac failure during the cortical mapping session of the first surgical procedure, most probably deriving from adverse effects of anesthesia. While rare, this cause of death is the most common reason for animal loss in similar experiments in our laboratory. GSK6 had not received any experimental injections prior to death.

Of the remaining seven monkeys, four monkeys were injected with Antibody A (GSK1, 3, 7, and 9; MS group) and three monkeys were given vehicle injections (GSK4, 5, and 8; VS group).

Infarct Size and Location

The intended target size of the infarcts in this study was 80% of the cortical territory containing representations of the distal forelimb in primary motor cortex (M1). For seven monkeys, the mean (±s.d.) size of the infarct area was 80.5±2.8%. Therefore, similarly to the rat studies described above, no neuroprotection was offered by Antibody A when administered 24 h following the onset of ischaemia.

Behaviour: Post-Infarct Performance

Figure 14:
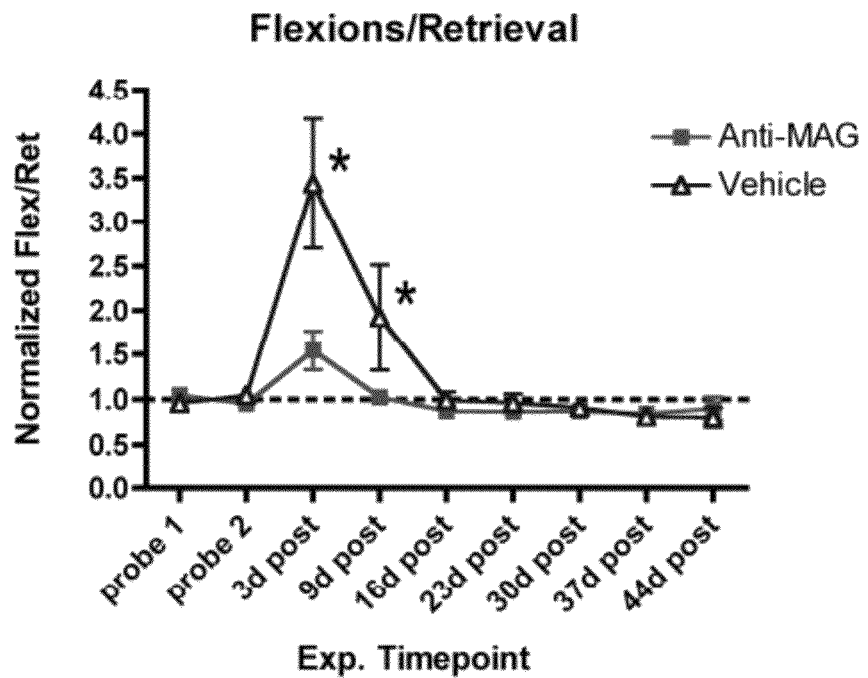
FIG. 14: Normalized flexions per retrieval illustrated for the two pre-infarct baseline probe tests (labelled "probe 1" and "probe 2" on graph) and the seven post-infarct probe tests. Asterisk indicates significant difference between groups (post-hoc test, p<0.05).
Figure 16:
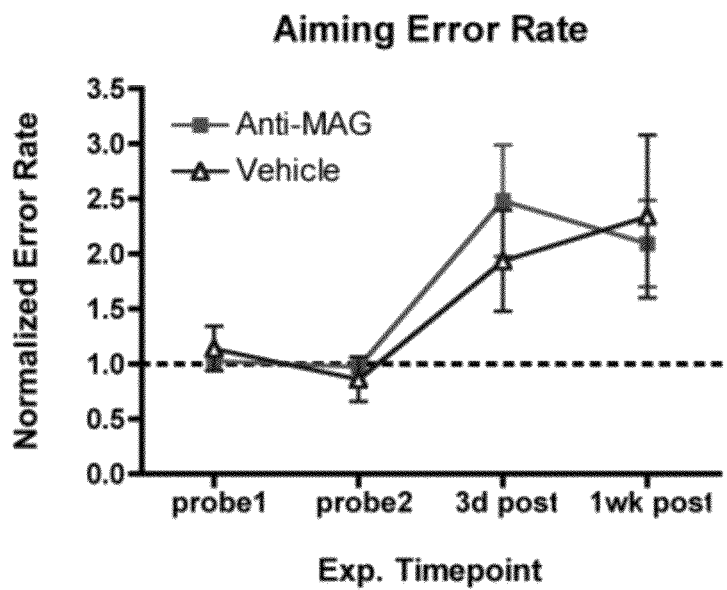
FIG. 16: Normalized rate of aiming errors illustrated for the two pre-infarct baseline probe tests (labelled "probe 1" and "probe 2" on graph) and the first two post-infarct probe tests.
Figure 15:
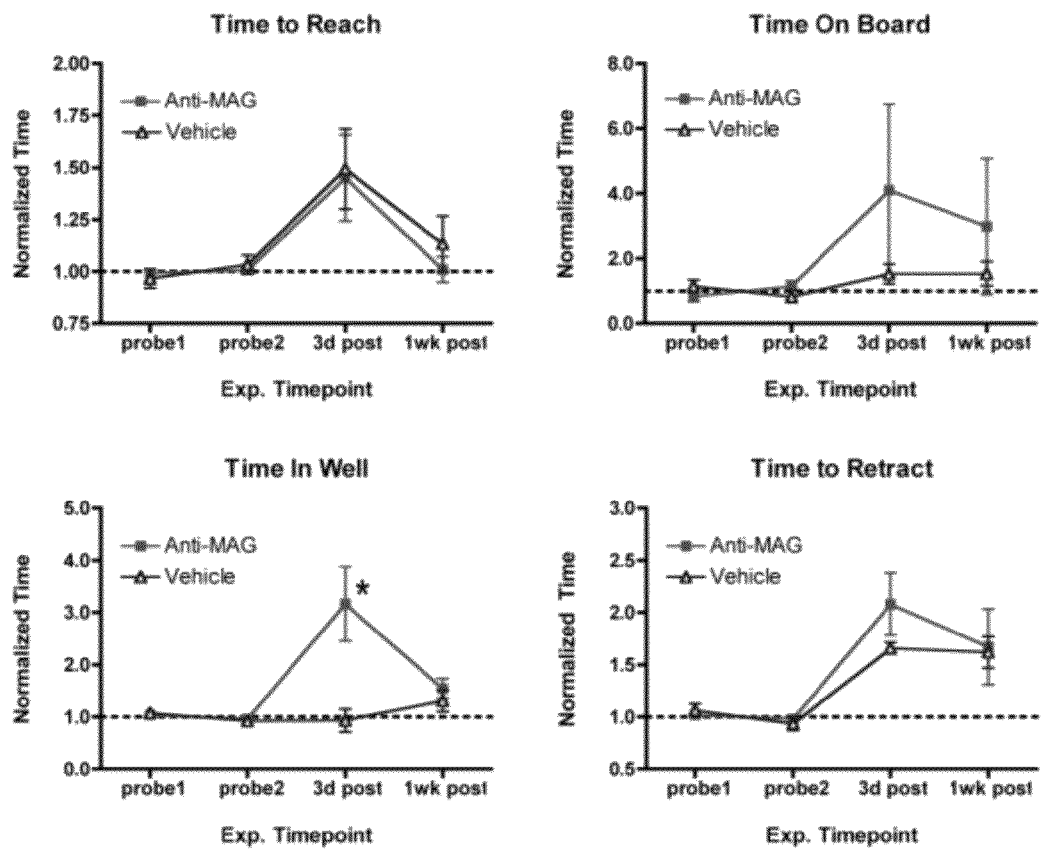
FIG. 15: Normalized retrieval time measures illustrated for the two pre-infarct baseline probe tests (labelled "probe 1" and "probe 2" on graph) and the first two post-infarct probe tests. Asterisk indicates significant difference between groups (post-hoc test, p<0.05).

Normalized baseline and post-infarct performance are illustrated in FIG. 14 (flexions/retrieval) and FIG. 15 (four retrieval time components), and FIG. 16 (aiming error rate). Of these six measures, three exhibited an effect of the infarct but were not differentially affected by the injection treatment.

Two of the behavioural measures, flexions/retrieval and time in well, exhibited significant group×time interactions in the ANOVAs, indicating a differential effect of experimental treatment. For flexions/retrieval, the Antibody A group increased from 1.00±0.09 at baseline to 1.55±0.43 at day 3 post-infarct, while the vehicle treated group increased from 1.00±0.08 at baseline to 3.44±1.26 at day 3 post-infarct. These changes produced significant effects of time ($F=8.02$, $p<0.001$) and significant group×time interaction ($F=3.06$, $p<0.001$). Bonferroni post-hoc tests revealed significant group differences for flex/ret at day 3 post-infarct ($t=7.09$, $p<0.001$). For time in well, the Antibody A treated group increased from 1.00±0.09 at baseline to 3.17±1.43 at day 3 post-infarct while the vehicle treated group decreased slightly from 1.00±0.11 at baseline to 0.93±0.38 at day 3 post-infarct. These changes produced significant effects of time ($F=5.54$, $p<0.01$) and a significant group×time interaction ($F=6.54$, $p<0.005$). Post-hoc tests indicated a group difference for time in well at day 3 post-infarct ($t=4.88$, $p<0.001$).

At week 1 post-infarct, flexions/retrieval remained significantly different between the Antibody A and vehicle treated groups (post-hoc, $t=3.36$, $p<0.05$), with a score of 1.02±0.16 for the Antibody A treated group and 1.92±1.03 for the vehicle treated group. Time in well was no longer different for the two groups at week 1 post-infarct (Antibody A, 1.55±0.38; vehicle, 1.31±0.37). By weeks 2 post-infarct, flex/ret measures had returned to pre-infarct levels for both groups.

Physiological Mapping Results

Pre-infarct motor maps of M1 and PMv were typical of the species. The mean (±s.d.) size of the M1 hand area was 13.81±1.67 mm$^2$ and the PMv hand area was 3.27±1.21 mm$^2$. The M1 hand area intentionally spared in the pre-infarct map was 2.65±0.50 mm$^2$ for the Antibody A treated group and 2.75±0.49 mm$^2$ for the vehicle treated group. The second ICMS map was derived at seven weeks (day 49) post-infarct, several days after the final behavioural data had been collected.

Figure 17:
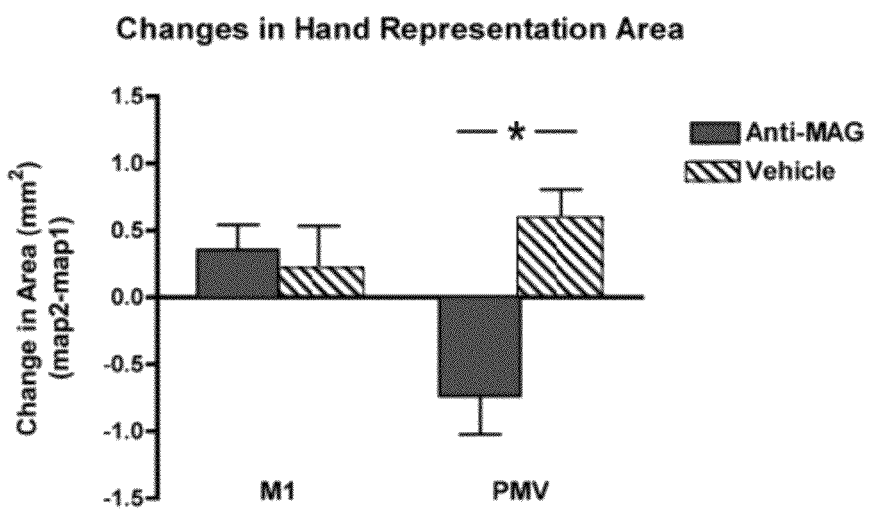
FIG. 17: Changes in size of hand area representations between the first (map1) and second (map2) ICMS derived motor maps for the spared, peri-infarct region (labelled "M1") and for PMv. There was a differential effect of treatment on map area in PMv (asterisk). Error bars are ±s.e.m.

In the second map, the spared hand area in peri-infarct M1 increased for both groups; by 0.35±0.38 mm$^2$ in the Antibody A group and by 0.18±0.62 mm$^2$ in the vehicle treated group (FIG. 17). These changes represent mean increases of 11.8% and 7.2% respectively. Repeated-measures ANOVA indicated no significant main effect of time or group×time interaction for the peri-infarct M1 changes. The hand area in PMv decreased in size by −0.74±0.58 mm$^2$ in the Antibody A treated group, a 19.2% loss (p=<0.084), and increased in size by 0.57±0.40 mm$^2$ in the vehicle treated group, a 17.5% gain. There was a significant group×time interaction for the PMv map changes (F=11.10, p<0.021), indicating that the injection treatment had a differential effect on physiological reorganization in PMv.

Conclusion

Difference in Behavioral Recovery Rates Between Drug and Vehicle Groups

The group receiving Antibody A displayed significantly better behavioural performance, as assessed by flexions/retrieval, on the reach-and-retrieve task compared with the vehicle control group at 3 d and 9 d post-infarct. Flexions/retrieval appeared to be at normal levels by 9 d in the MS group versus by 16 d in the VS group. Conversely, the MS group exhibited significantly slower pellet extraction movements, as indicated by time in well, at 3 d post-infarct compared to the VS group. Values for time in well were similar at 9 d for both groups. Although group differences in behavioural performance resolved by 16 d post-infarct, it appears that Antibody A had behavioural consequences soon after administration.

The pattern of differences in behavioural performance at 3 d post-infarct between the MS group (minimal flexions/retrieval impairment, substantial time in well impairment) and the VS group (substantial flexions/retrieval impairment, minimal time in well impairment) are suggestive of a strategic speed-accuracy trade-off (referred to generally as Fitts' law). For example, by slowing down the flexion movement, monkeys might achieve improved control of the pellet, thus requiring overall fewer flexions to successfully remove pellets from the well. Alternatively, faster flexions might have produced poorer control and thus more flexions to achieve success. However, at 9 d post-infarct, time in well values were similar for both groups but the VS group was still significantly impaired in flexions/retrieval. So, even if the group difference at 3 d reflects a Fitts' law effect, the outcomes at 9 d indicate that Antibody A had a positive benefit on performance in the MS group, facilitating recovery of both movement speed and accuracy.

Differences in Physiological Maps Between Drug and Vehicle Groups

In peri-infarct cortex in M1, although there was a small increase in hand representation in both groups, these increases were not significant, nor was there a difference between the two groups.

In PMv, an unexpected and unusual result was found. For the VS group, the PMv hand representation was substantially expanded, consistent with a prior study examining PMv after M1 infarct and spontaneous recovery (SB Frost, et al., (2003) "Reorganization of remote cortical regions after ischemic brain injury: a potential substrate for stroke recovery", Journal of Neurophysiology, 89:3205-3214). However, the PMv hand area in the MS group was substantially reduced in size, resulting in a significant difference between the two groups. This finding indicates that despite similarities in behavioural performance at the time of map derivation (seven weeks post-infarct), behavioural recovery was associated with different patterns of physiological reorganization in the two groups. The reduction of PMv hand area in the MS group suggests that the normal dynamics of post-infarct interaction between PMv and M1 may have been affected by administration of anti-MAG. It also suggests that an unexamined brain region(s) may play a larger role in behavioural recovery to compensate for the reduced role of PMv.

The results of this study indicate that Antibody A significantly enhanced functional recovery and also neurophysiological reorganization following a focal ischemic infarct in motor cortex of squirrel monkeys as compared to vehicle treated animals. The present results support prior studies demonstrating efficacy of Antibody A in rodent models of stroke as outlined above, extending these findings into a non-human primate. This further support the rationale for dosing Antibody A following the acute period post stroke.

Example 8

Calculation of $C_{max}$ and AUC

Analysis of Human Plasma Samples

The method for the determination of Antibody A plasma concentrations in human plasma is a chemiluminescent immunoassay. The method is selective for Antibody A and has a validated range of 50 to 2500 ng/mL.

Plasma samples are diluted 11 fold in assay buffer prior to analysis. Antibody A is captured using monomeric human MAG coated on a microtiter plate and detected using horse radish peroxidase labelled mouse anti-human IgG1 specific for the Fc region. Chemiluminescent immunoassay data are acquired using a microtiterplate reader. Concentrations of Antibody A in the human plasma samples are determined from a calibration curve constructed with known concentrations of Antibody A across the assay range (50 to 2500 ng/mL). Samples that are above the upper limit of quantification of the assay (2500 ng/mL) are diluted into the assay range with assay buffer containing 9.09% human plasma. The acceptance of each analytical run is assessed using quality control (QC) samples (n=4) at three concentrations. For the run to be accepted, at least 8 out of 12 of all the QC samples, and at least two at each of the three concentrations, must be within +/−20% of their known concentration.

Results

Figure 18:
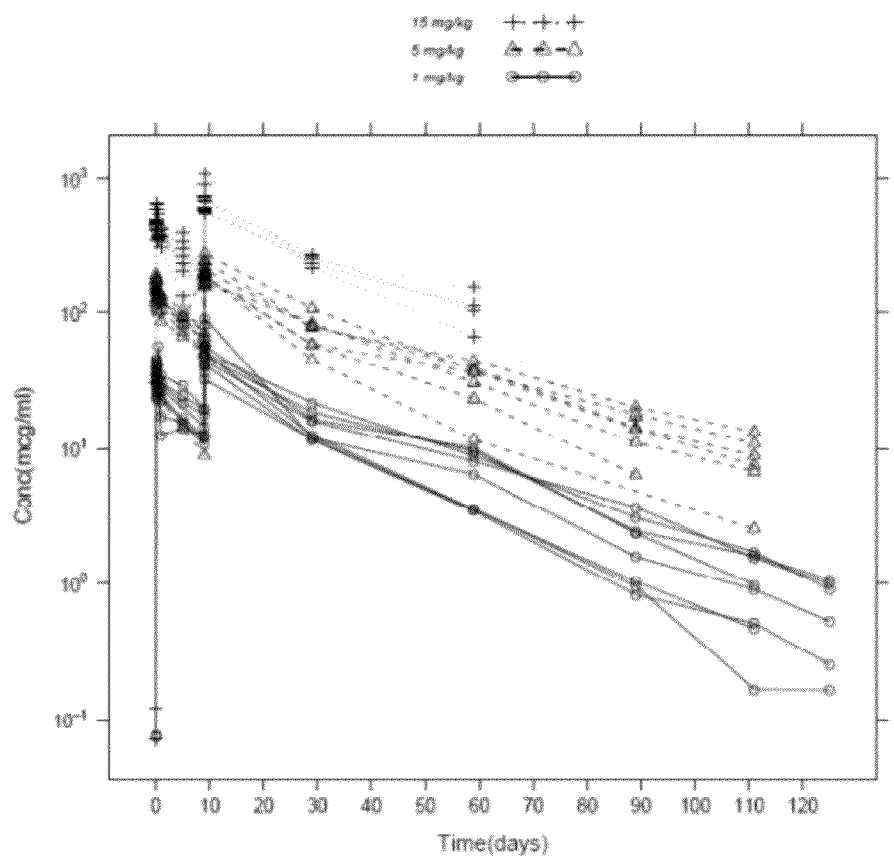
FIG. 18: Raw data of plasma concentrations for use in calculating $C_{max}$ at a dose of 1, 5 and 15 mg/kg.

Data was obtained by this method in patients who had received two individual doses of Antibody A, 9±1 days apart, at individual doses of 1 mg/kg, 5 mg/kg or 15 mg/kg. FIG. 18 shows the raw data which was processed.

A: Calculation of $C_{max}$ for Two Doses Each at 1 mg/kg, 5 mg/kg and 15 mg/kg $C_{max}$ values are obtained by the Non Compartmental Analysis performed using Winnonlin v 5.2 (available from Pharsight) on the dataset shown in FIG. 18.

B: Calculation of $AUC_{(0-Inf)}$ for Two Doses Each at 1 mg/kg, 5 mg/kg and 15 mg/kg To calculate the $AUC_{(0-inf)}$ values for the data above (i.e. for two doses of Antibody A at 1, 5 and 15 mg/kg doses), a two-compartment model was used, with NONMEM 6 software (ICON Development Solutions may license the use, courtesy of Regents of the University of California) using Script 1 which is provided in FIG. 19, on the dataset shown in FIG. 18. AUC(0-inf) was defined as the AUC(0-inf) after a single dose and calculated as DOSE/CL (with DOSE equal to 1, 5 or 15 mg/kg).

C: Simulation of $C_{max}$ and $AUC_{(0-inf)}$ for Doses of 0.1 mg/kg and 25 mg/kg Simulations were performed to generate 1000 anti-MAG concentration profiles using the above model (Part B, FIG. 19) and its final parameter estimates (THETA: CL=0.0726 ml/kg/h, V2=20.6 ml/kg, V1=31.3 ml/kg, DVZ=2.93; OMEGA: 0.0427, 0.14 0.0225, 0.0894; SIGMA 0.0224), both at doses of 0.1 mg/kg and 25 mg/kg, in two repeated administrations 9 days apart. $C_{max}$ was obtained from the simulated concentration at the end of the second repeated infusion and $AUC_{(0-inf)}$ was calculated as DOSE/CL (with DOSE equal to 0.1 or 25 mg/kg).

D: Confidence Intervals

The 95% confidence intervals of $C_{max}$ and AUC values in all the different scenarios (i.e. from part A, B and C) were calculated using software R, version 2.10.1, where the min was derived using the function:

$FLB=\text{function}(x)\{\exp(\text{mean}(\log(na \cdot \text{omit}(x)))-1.96*sd(\log(na \cdot \text{omit}(x))))\}$ and the max, using the function:

$FUB=\text{function}(x)\{\exp(\text{mean}(\log(na \cdot \text{omit}(x)))+1.96*sd(\log(na \cdot \text{omit}(x))))\}$ E: Exemplary Parameter Values Exemplary parameter values were calculated using software R, version 2.10.1 as the geometric mean of the parameter in the considered group of subjects Results

| Doses (mg/kg) | $C_{max}$ (mcg/ml) (95% CI) | $AUC_{(0-inf)}$ (mg/ml h) (95% CI) |
|---|---|---|
| 1 | 50.8 (27.7 – 93.1) | 13.6 (8.4 – 21.8) |
| 5 | 213.9 (164.4 – 278.5) | 66.8 (47.7 – 93.5) |
| 15 | 740.6 (480.3 – 1142.2) | 216.6 (166.9 – 281.2) |
| 1-15 | 27.7 – 1142.2 | 8.4 – 281.2 |
| 0.1-25 | 3.0 – 1666.8 | 0.9 – 517.8 |

^when a dose range is specified, only the parameter interval is defined which ranges from the minimum of the CI of the lowest dose to the maximum of the CI of the maximum dose Example 9

Simulated Pharmacodynamics of Doses of Anti-MAG Antibody Comparing One Vs Two Doses Simulations for this example were performed using the above model (Example 8, Part B, FIG. 19) and its final parameter estimates (as in Example 8, Part C) and a dosing scheme of 15 mg/kg in two repeated administrations, 9 days apart and 30 mg/kg in single dose.

Figures 19, 20:
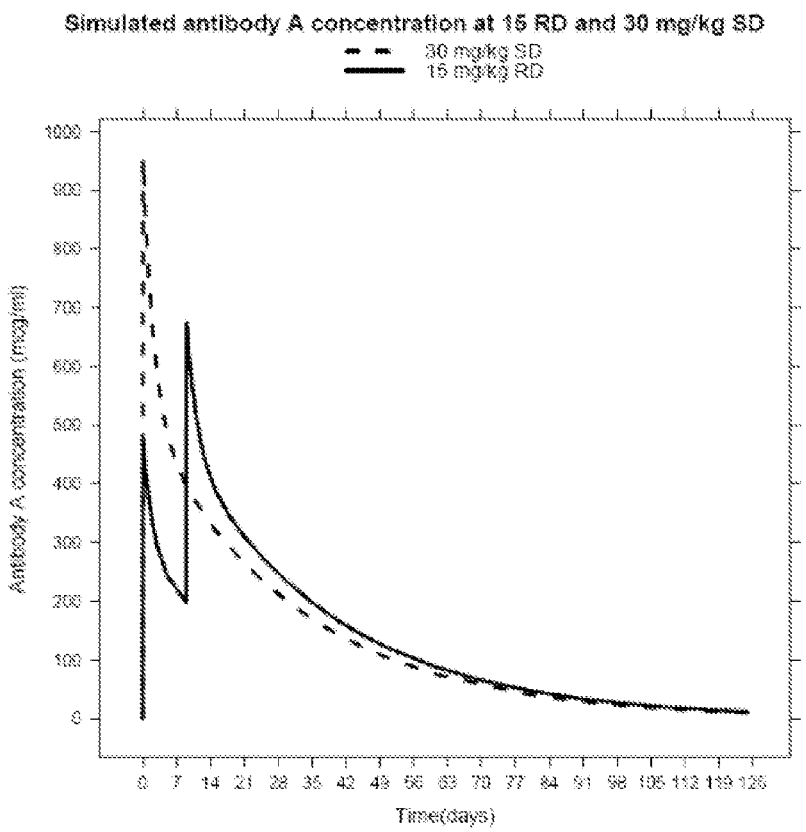
FIG. 19: NONMEM Script 1 for use in calculating $AUC_{(0\text{-}inf)}$ at a dose of 1, 5 and 15 mg/kg, in which CL is the clearance in mL/kg/h, V1 is the volume of the central compartment in ml/kg, V2 is the volume of the peripheral compartment in mL/kg, DVZ is the volume at the terminal state, VZ, minus the Volume at steady state, VSS, ID is Identification Number, SBJ is subject number, TIME is time in hours, DV is data value in µg/mL, i.e. the plasma concentration obtained from that subject at that timepoint, DAY is the day, WK is the week, DOSE is the dose administered to the patient in mg/kg, coho is cohort number, MDV is missing data value (true/false), AMT is amount in µg/mL, RATE is infusion rate, ADDL is the number of additional doses, II is the interdose interval in hours and EVID is event ID.
FIG. 20: Simulation of PK profile for one dose of 30 mg/kg administered in one dose as compared to two doses of 15 mg/kg administered nine days apart as depicted graphically.

FIG. 20 shows the graphical representation of the plot of these data as obtained using software R, version 2.10.1.

This data shows that the $C_{max}$ is likely to be lower when administering the same dose over two administrations, with the result of a likely reduction in side effects. It also shows that because of the properties of Antibody A, it is expected that a similar AUC and hence efficacy profile will be obtained.

Example 10

A Single-Blind Study of the Safety, Pharmacokinetics and Pharmacodynamics of Escalating Repeat Doses of Antibody A in Patients with Stroke Methodology This study was a placebo-controlled, single-blind, multi-centre, randomized study to investigate the safety, PK and PD of escalating repeat IV doses of Antibody A in subjects with stroke. The study was also designed to collect serial data on several functional and neurophysiological outcome measures. While the study was single blind, all subjects, site staff (except for the pharmacist) and GlaxoSmithKline (GSK) staff were blinded to treatment.

Three dose escalation cohorts were planned, with a 1:1 randomization ratio in cohort 1 (8 planned subjects on Antibody A, and 8 on placebo) and a 2:1 ratio in each of cohorts 2 and 3 (8 planned subjects on Antibody A and 4 on placebo) for a total of 40 subjects enrolled. A Dose Escalation Committee (DEC) reviewed key safety data from a cohort before escalation to the next highest dosing cohort occurred.

Each subject was to receive two IV doses 9±1 days apart, where the first dose was administered 24-72 hours post stroke. Assessments extended to at least 16 weeks. Provision was made for subjects to remain in the study until circulating levels of Antibody A fell to a threshold which was suitable to allow for testing of antibodies to Antibody A. Table 3 describes the maximum length of time subjects in each cohort could have remained in the study.

TABLE 3

| Cohort | Dose | Length of Observation Period |
|---|---|---|
| 1 | 1 mg/kg | 126 days |
| 2 | 5 mg/kg | 175 days |
| 3 | 15 mg/kg | 210 days |

Pharmacokinetic Assessments

PK samples were collected at the following time points: pre-dose, 1 hr post-first dose, 3 h post-first dose, 6 h post-first dose, 12 h post-first dose, 24 h post-first dose, on study day 5±1 day, on study day 10±1 day (pre-second dose) and at 1 h post-second dose and 3 h post-second dose, and on study day 30±3 days, study day 60±3 days, study day 90±3 days and study day 112±3 days. Samples were collected at nominal times relative to the proposed time of Antibody A dosing.

Plasma samples were analyzed for Antibody A using a validated analytical method based on sample dilution, followed by immunoassay analysis. The lower limit of quantification (LLQ) was 50 ng/mL using a 100 µL aliquot of EDTA plasma. The higher limit of quantification (HLQ) was 2500 ng/mL.

For each analytical method, quality control samples (QC), containing Antibody A at 3 different concentrations and stored with study samples, were analyzed with each batch of samples against separately prepared calibration standards. For the analysis to be acceptable, no more than one-third of the QC results were to deviate from the nominal concentration by more than 20%, and at least 50% of the results from each QC concentration should be within 20% of nominal. The applicable analytical runs met all predefined run acceptance criteria.

Statistical Analysis

An initial assessment of dose proportionality was explored for AUC from time zero (pre-dose) extrapolated to infinite time ($AUC_{(0-inf)}$, AUC from time zero (pre-dose) to last time of quantifiable concentration within a subject across all treatments ($AUC_{(0-t)}$) where $AUC_{(0-t)}$ coincides with AUC over the dosing interval from 0 to Day 10±1 day ($AUC_{(0-10d)}$) after the first administration, and $C_{max}$ using graphical presentations. Scatter plots of log $AUC_{(0-inf)}$, log $AUC_{(0-t)}$ and log $C_{max}$ against log dose were produced.

An assessment of dose proportionality was made on $AUC_{(0-inf)}$, $AUC_{(0-t)}$, and $C_{max}$ using the Power Model (See RAP, Section 11.4).

Non-Compartmental Analyses

All calculations of non-compartmental parameters were based on actual sampling times. The PK parameters were calculated by standard non-compartmental analysis according to current working practices and using WinNonlin Pro 4.1.

Derived parameters were the AUC extrapolated to infinity after a single dose ($AUC_{(0-inf)}$) and the clearance (CL). $AUC_{(0-inf)}$ was calculated, where data permitted, as the sum of $AUC_{(0-t)}$ after the first administration and Ct after the first administration divided by λz, where Ct is the last observed plasma concentration before the second administration, mainly coinciding with the concentration at Day 10, and λz is the terminal phase rate constant calculated after the second administration. CL was derived as Dose divided by $AUC_{(0-inf)}$.

Functional and Neurophysiological Assessments: Gait Velocity

Gait velocity is an objective, quantitative measure of lower extremity motor recovery that has been shown to be reliable, valid and sensitive in the stroke population [Richards, 1995]. Additionally changes in gait velocity have been shown to correlate with physical functioning and quality of life [Perry, 1995; Schmid, 2007].

Gait velocity was assessed over a level, indoor 10 meter distance. The time (in seconds) it took the subject to travel the 10 meter distance was recorded. Subjects were asked to walk at their usual or normal pace and may have used their normal assistive devices. Two trials of gait velocity were conducted on study day 5±1 day, study day 30±1 day, study day 60±3 days, study day 90±3 days and study day 112±3 days.

Other functional and neurophysiological assessments were made during this study, which are well-known to those skilled in the art. They were: Berg Balance Scale, Fugl-Meyer Motor Assessment, Box and Blocks Test, Grip Strength (dynamometer), Transcranial Magnetic Stimulation, Magnetic Resonance Imaging, Modified Rankin Scale, NIH Stroke Scale, Barthel, Montreal Cognitive Assessment, and Geriatric Depression Scale.

Results

While not powered to demonstrate efficacy, gait velocity data from this study suggest a trend toward benefit with Antibody A treatment which warrants further exploration. NIHSS total scores improved over time showing neurological improvement and no evidence of harm over time with Antibody A treatment. There were no apparent trends across all of the PD functional and the neurophysiological measures that might be suggestive of a clinical worsening in those subjects who received Antibody A.

Gait Velocity

In the repeated measures analysis of change in mean gait velocity, there was a trend towards improvement with greater increases over time in the adjusted mean gait velocity from baseline in the Antibody A dose groups compared with placebo (Table 4).

TABLE 4

Summary of Mixed Model Repeated Measures Analysis of Change in Mean Gait Velocity (All Subjects Population

| Visit/Comparison | Adjusted Mean | | Treatment Difference (SE) | 95% CI |
| --- | --- | --- | --- | --- |
| | Antibody A | Placebo | | |
| Visit 4 Day 30 | | | | |
| Antibody A 1 mg/kg vs placebo | 0.44 | −0.01 | 0.45 (0.231) | (−0.03, 0.92) |
| Antibody A 5 mg/kg vs placebo | 0.68 | −0.01 | 0.69 (0.214) | (0.25, 1.13) |
| Antibody A 15 mg/kg vs placebo | 0.29 | −0.01 | 0.30 (0.246) | (−0.20, 0.80) |
| Visit 5 Day 60 | | | | |
| Antibody A 1 mg/kg vs placebo | 0.59 | 0.24 | 0.35 (0.292) | (−0.24, 0.95) |
| Antibody A 5 mg/kg vs placebo | 0.76 | 0.24 | 0.52 (0.279) | (−0.05, 1.09) |
| Antibody A 15 mg/kg vs placebo | 0.28 | 0.24 | 0.04 (0.319) | (−0.61, 0.69) |
| Visit 6 Day 90 | | | | |
| Antibody A 1 mg/kg vs placebo | 0.84 | 0.21 | 0.63 (0.235) | (0.15, 1.11) |
| Antibody A 5 mg/kg vs placebo | 0.61 | 0.21 | 0.40 (0.225) | (−0.06, 0.86) |
| Antibody A 15 mg/kg vs placebo | 0.45 | 0.21 | 0.24 (0.259) | (−0.29, 0.77) |
| Visit 7 Day 112 | | | | |
| Antibody A 1 mg/kg vs placebo | 0.97 | 0.36 | 0.61 (0.251) | (0.10, 1.12) |
| Antibody A 5 mg/kg vs placebo | 0.94 | 0.36 | 0.59 (0.242) | (0.09, 1.08) |
| Antibody A 15 mg/kg vs placebo | 0.53 | 0.36 | 0.17 (0.277) | (−0.39, 0.73) |

The following other functional and neurophysiological assessments also showed a trend towards improvement with greater mean changes from baselines in at least one of the dose groups compared with placebo: Berg Balance Scale and Fugl-Meyer Motor Assessment.

The following assessments showed no statistically significant difference between placebo and treatment groups with respect to the adjusted mean changes: Box and Blocks Test, Grip Strength (Dynamometer), Transcriptional Magnetic Stimulation, NIH Stroke Scale, Modified Rankin Scale, Barthel, Montreal Cognitive Assessment and Geriatric Depression Scale. No meaningful conclusion could be drawn on any reduction in lesion volume as measured by Magnetic Resonance Imaging.

Pharmacokinetic Assessment $AUC_{(0-inf)}$ and $C_{max}$ were calculated as described and the results obtained were comparable to that predicted and reported in Example 8.

Example 11

Comparison of Serum Soluble Myelin Associated Glycoprotein Levels in Healthy Donors Compared to Ischemic Patients from the Clinical Study Reported in Example 10

Methods

Serum samples from the clinical trial reported in Example 10 were stored at −80° C., and thawed no longer than 30 minutes before use in the soluble MAG assay. All antibodies and proteins were produced in house and dissolved in PBS.

Soluble MAG Mesoscale Discovery (MSD) assay was set up to measure soluble (unbound) MAG fragments in serum. MSD plates were spot coated with 1 μL/well 50 μg/mL Antibody A in buffer (25 mM Hepes, 0.015% Triton X-100). Once dry, plates were blocked with 150 μL/well 3% MSD blocker A (MSD #R93BA) for an hour then washed with PBS 0.05% Tween 20, and MSD serum cytokine assay diluent (MSD #R51BB) added for 30 minutes. GSK Human recombinant MAG (extracellular domain) was used as the standard. A standard curve was prepared in MAG depleted pooled human serum from 4.88-5000 pg/mL. Standards/samples (25 μL/well) and detection antibody solution (25 μL/well) (MSD sulfo-TAG labelled GSK mouse anti human MAG monoclonal antibody) were added and incubated for 4 hours. Plates were then washed, as above. 2×MSD read buffer T was then added (150 μL/well). Plates were then read immediately on the MSD Sector Imager 6000.

MSD raw counts were back calculated to a standard curve which was ran on each individual assay plate. Data was back-calculated using XLfit software version 5.1.0.0. A dose response one-site four parameter logistic curve model was fitted to the standard curve data to estimate parameters A, B, C and D using the following formula (fit 204 in XLFit):

$$\text{Log(count)} = (A + ((B-A)/(1+(10^{((C-\log(\text{conc}))*D)}))))$$

Using this formula, sample concentrations are back calculated from sample counts using the following formula:

$$\text{Log(conc)} = (C - (\log(((B-A)/(\log(\text{count})-A))-1)/D))$$

Array studio, version 5.0.0.45, was also used to analyse the data.

Results

Soluble MAG Assay Parameters

Figure 21:
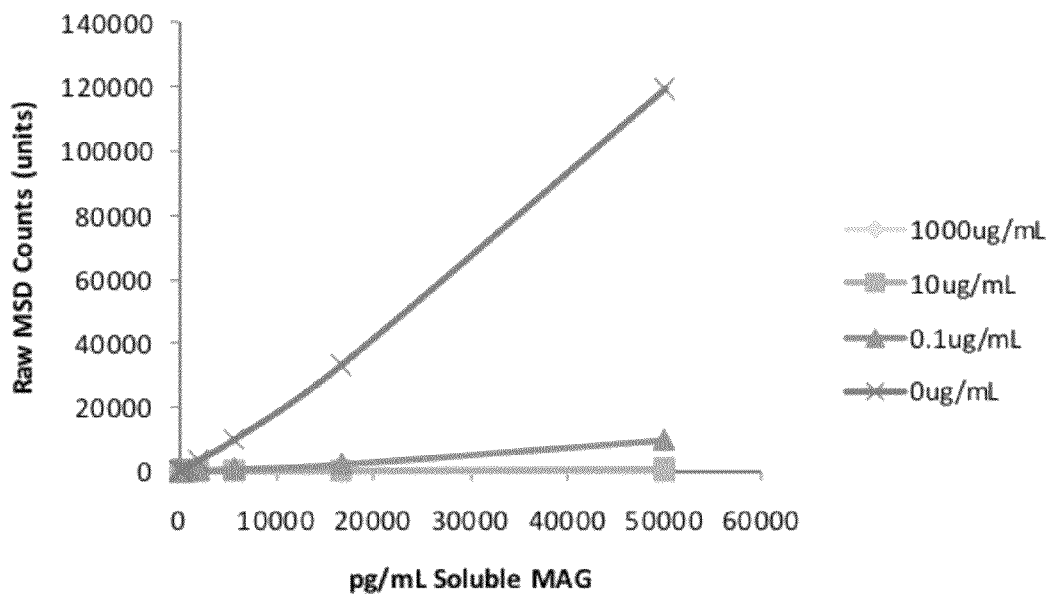
FIG. 21: Titration of Drug into Soluble MAG assay of Example 11. Drug was titrated into the soluble MAG assay standard curve at three concentrations (0.1, 10 and 1000 µg/mL), and incubated for an hour before addition to the assay.

Antibody A was titrated into the soluble MAG assay standard curve at three concentrations (0.1, 10 and 1000 μg/mL), and incubated for an hour before addition to the assay. The MSD signal was fully quenched with 10 and 1000 μg/mL of drug, providing evidence that when MAG is complexed with drug it cannot be measured in this assay format hence the assay measures "Antibody A free" soluble MAG (FIG. 21).

Healthy Subject Results

Soluble MAG was detected at low levels in a number of healthy subjects, the mean MAG level was 9.64+/−15.29 pg/mL (n=56). However once samples below the lower limit of quantification (LLOQ, estimated at 4.88 pg/mL) have been removed the mean MAG level rises to 22.16+/−20.43 pg/mL (n=20, range from 5-67 pg/mL).

Ischemic Stroke Patient Results for the Clinical Study Reported in Example 10

Figure 22:
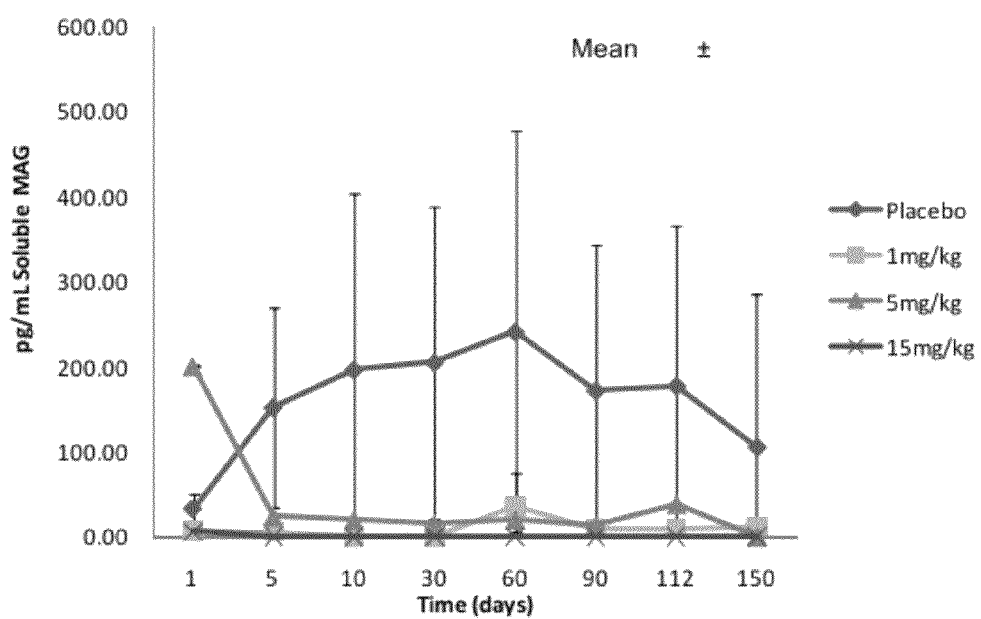
FIG. 22: Soluble MAG Levels for the Clinical Study reported in Example 10. Mean time course of soluble MAG (pg/mL±95% CI) for all four cohorts (placebo, 1, 5 and 15 mg/kg) of the reported study. Samples below the LLOQ (4.88 pg/mL) have been removed from the mean data.

In the clinical study reported in Example 10, mean data from each of the cohorts showed low levels of soluble MAG at the initial timepoint (24-72 hours post the onset of ischaemia). However, in the placebo group, mean levels of MAG increase over time and remain elevated for most of the study in comparison to all the dosed groups which showed low or undetectable levels of MAG immediately post dosing [FIG. 22]. Review of the individual patient placebo data showed that from day 5 to 10, 6 out of 15 subjects showed an increase in MAG levels post stroke, ranging from a 59 pg/mL to 577 pg/mL peak. The other 9 placebo subjects did not show this trend, with the majority of samples being below the lower limit of quantification (LLOQ) for the assay, estimated at 4.88 pg/mL.

Figure 23:
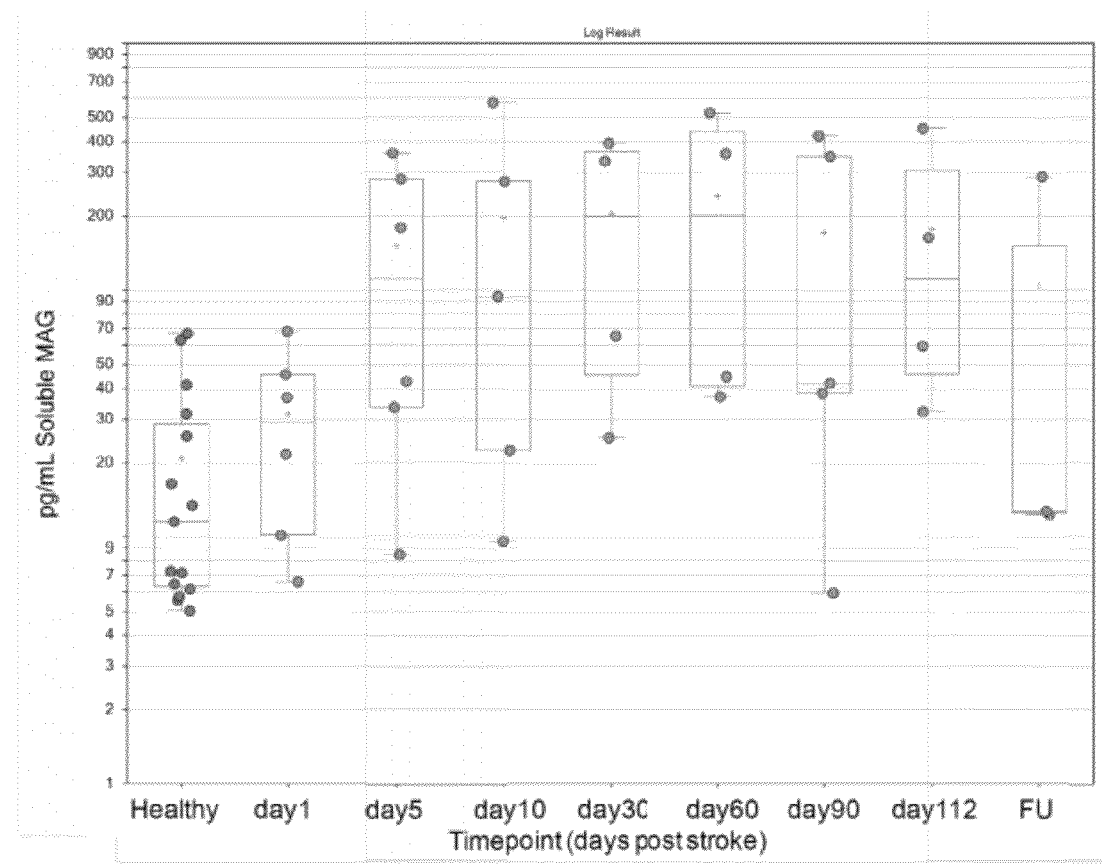
FIG. 23: Timecourse Free Soluble MAG from Placebo-Treated Stroke Subjects, compared with healthy donors (left column). Time course of soluble MAG expression (±95% CI) in healthy subjects (n=36) and timecourse of soluble MAG expression in placebo treated stroke subjects (n=15). Samples below the LLOQ (4.88 pg/mL) have been removed.

Plotting of the placebo group data on a Log 2 scale clearly shows no difference in soluble MAG levels between healthy donor and stroke patients at the initial timepoint (24-72 hours post the onset of ischaemia) [FIG. 23]. Soluble MAG levels increased between 5 to 10 days post stroke and remained elevated for 4 to 5 months and started to drop around the follow up timepoint (approximately 150 days post stroke).

Very few subjects within the dosed cohorts showed levels of MAG above the LLOQ before dosing (day 1). Subjects within the 1 mg/kg cohort had very low levels of MAG until day 60 where two subjects show increasing levels of MAG. The higher dosed cohorts (5 and 15 mg/kg) did not show this increase, the MAG levels within these subjects stayed below the LLOQ throughout the timecourse. The data clearly show a reduction in soluble MAG in the dosed subjects which appears to be dose dependent.

---

The invention claimed is:

1. A method of treating stroke comprising intravenous administration of an anti-MAG antibody to a human patient in need thereof in two doses
wherein,
   i) the anti-MAG antibody comprises a heavy chain variable region comprising the sequence of SEQ ID NO:10 and a light chain variable region comprising the sequence of SEQ ID NO:14;
   ii) the first dose of the anti-MAG antibody is administered up to 3 days after the onset of stroke;
   iii) the second dose of the anti-MAG antibody is administered between 3 and 10 days after the first dose; and
   iv) wherein the first and second doses result in an improvement in the adjusted mean gait velocity of the patient.

2. A method according to claim 1, wherein the dose administered to the patient on each occasion is from 0.1 mg/kg to 25 mg/kg.

3. A method according to claim 1, wherein the dose administered to the patient on each occasion is selected from 1 mg/kg, 5 mg/kg and 15 mg/kg.

4. A method according to claim 1 wherein the anti-MAG antibody is humanised.

5. A method according to claim 1, wherein the stroke is ischemic stroke.

6. A method according to claim 1, wherein the stroke is haemorrhagic stroke.

7. A method according to claim 1, wherein the first dose is administered between 24 and 72 hours post-stroke.

8. A method according to claim 7, wherein the second dose is administered between 8 and 10 days after the first dose.

9. A method according to claim 1, wherein the anti-MAG antibody is administered after dilution from an aqueous composition comprising 50 mM sodium acetate, 104.4 mM sodium chloride and 0.02% by weight Polysorbate 80, and wherein the pH is about 5.5.

10. A method according to claim 1, wherein each dose is independently administered to the patient by intravenous infusion over a period of up to 60 minutes.

11. A method according to claim 1, wherein the anti-MAG antibody provides an AUC(0-inf) value of between 8.4-281.2 mg/mL h±10%.

12. A method according to claim 1, wherein the anti-MAG antibody provides an AUC(0-inf) value selected from one of the following: between 8.4-21.8 mg/mL h±10%; between 47.7-93.5 mg/mL h±10%; between 166.9-281.2 mg/mL h±15%; approximately 13.6 mg/mL h±10%; approximately 66.8 mg/mL h±10% or approximately 216.6 mg/mL h±15%.

13. A method according to claim 1, wherein the anti-MAG antibody provides a $C_{max}$ value of between 27.7-1142.2 mg/mL h±10%.

14. A method according to claim 1, wherein the anti-MAG antibody provides a $C_{max}$ value selected from one of the following: between 27.7-93.1 mg/mL h±10%; between 164.4-278.5 mg/mL h±10%; between 480.3-1142.2 mg/mL h±10%; approximately 50.8 µg/mL±10%; approximately 213.9 µg/mL±10%; or approximately 740.6 µg/mL±10%.

* * * * *

SEQUENCE LISTING

```
<160> NUMBER OF SEQ ID NOS: 19

<210> SEQ ID NO 1
<211> LENGTH: 17
<212> TYPE: PRT
<213> ORGANISM: Artificial Sequence
<220> FEATURE:
<223> OTHER INFORMATION: CDRL1

<400> SEQUENCE: 1

Lys Ser Ser His Ser Val Leu Tyr Ser Ser Asn Gln Lys Asn Tyr Leu
1               5                   10                  15

Ala

<210> SEQ ID NO 2
<211> LENGTH: 7
<212> TYPE: PRT
```

```
<213> ORGANISM: Artificial Sequence
<220> FEATURE:
<223> OTHER INFORMATION: CDRL2

<400> SEQUENCE: 2

Trp Ala Ser Thr Arg Glu Ser
 1               5

<210> SEQ ID NO 3
<211> LENGTH: 8
<212> TYPE: PRT
<213> ORGANISM: Artificial Sequence
<220> FEATURE:
<223> OTHER INFORMATION: CDRL3

<400> SEQUENCE: 3

His Gln Tyr Leu Ser Ser Leu Thr
 1               5

<210> SEQ ID NO 4
<211> LENGTH: 5
<212> TYPE: PRT
<213> ORGANISM: Artificial Sequence
<220> FEATURE:
<223> OTHER INFORMATION: CDRH1

<400> SEQUENCE: 4

Asn Tyr Gly Met Asn
 1               5

<210> SEQ ID NO 5
<211> LENGTH: 17
<212> TYPE: PRT
<213> ORGANISM: Artificial Sequence
<220> FEATURE:
<223> OTHER INFORMATION: CDRH2

<400> SEQUENCE: 5

Trp Ile Asn Thr Tyr Thr Gly Glu Pro Thr Tyr Ala Asp Asp Phe Thr
 1               5                  10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: CDRH3

<400> SEQUENCE: 6

Asn Pro Ile Asn Tyr Tyr Gly Ile Asn Tyr Glu Gly Tyr Val Met Asp
 1               5                  10                  15

Tyr

<210> SEQ ID NO 7
<211> LENGTH: 475
<212> TYPE: PRT
<213> ORGANISM: Homo sapien

<400> SEQUENCE: 7

Met Gly Trp Ser Cys Ile Ile Leu Phe Leu Val Ala Thr Ala Thr Gly
 1               5                  10                  15

Val His Ser Glu Ile Gln Leu Val Gln Ser Gly Pro Glu Leu Lys Lys
                20                  25                  30
```

-continued

Pro Gly Glu Thr Asn Lys Ile Ser Cys Lys Ala Ser Gly Tyr Thr Phe
       35                  40                  45

Thr Asn Tyr Gly Met Asn Trp Val Lys Gln Ala Pro Gly Lys Gly Leu
   50                  55                  60

Lys Trp Met Gly Trp Ile Asn Thr Tyr Thr Gly Glu Pro Thr Tyr Ala
65                  70                  75                  80

Asp Asp Phe Thr Gly Arg Phe Ala Phe Ser Leu Glu Thr Ser Ala Ser
               85                  90                  95

Thr Ala Tyr Leu Gln Ile Ser Asn Leu Lys Asn Glu Asp Thr Ala Thr
           100                 105                 110

Tyr Phe Cys Ala Arg Asn Pro Ile Asn Tyr Tyr Gly Ile Asn Tyr Glu
       115                 120                 125

Gly Tyr Val Met Asp Tyr Trp Gly Gln Gly Thr Leu Val Thr Val Ser
   130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
               165                 170                 175

Tyr Phe Pro Glu Pro Val Thr Val Ser Trp Asn Ser Gly Ala Leu Thr
           180                 185                 190

Ser Gly Val His Thr Phe Pro Ala Val Leu Gln Ser Ser Gly Leu Tyr
       195                 200                 205

Ser Leu Ser Ser Val Val Thr Val Pro Ser Ser Ser Leu Gly Thr Gln
   210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
               245                 250                 255

Cys Pro Ala Pro Glu Leu Ala Gly Ala Pro Ser Val Phe Leu Phe Pro
           260                 265                 270

Pro Lys Pro Lys Asp Thr Leu Met Ile Ser Arg Thr Pro Glu Val Thr
       275                 280                 285

Cys Val Val Val Asp Val Ser His Glu Asp Pro Glu Val Lys Phe Asn
   290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
               325                 330                 335

Leu His Gln Asp Trp Leu Asn Gly Lys Glu Tyr Lys Cys Lys Val Ser
           340                 345                 350

Asn Lys Ala Leu Pro Ala Pro Ile Glu Lys Thr Ile Ser Lys Ala Lys
       355                 360                 365

Gly Gln Pro Arg Glu Pro Gln Val Tyr Thr Leu Pro Pro Ser Arg Asp
   370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
               405                 410                 415

Asn Asn Tyr Lys Thr Thr Pro Pro Val Leu Asp Ser Asp Gly Ser Phe
           420                 425                 430

Phe Leu Tyr Ser Lys Leu Thr Val Asp Lys Ser Arg Trp Gln Gln Gly
       435                 440                 445

Asn Val Phe Ser Cys Ser Val Met His Glu Ala Leu His Asn His Tyr

```
                    450                 455                 460
Thr Gln Lys Ser Leu Ser Leu Ser Pro Gly Lys
465                 470                 475

<210> SEQ ID NO 8
<211> LENGTH: 238
<212> TYPE: PRT
<213> ORGANISM: Homo sapien

<400> SEQUENCE: 8

Met Gly Trp Ser Cys Ile Ile Leu Phe Leu Val Ala Thr Ala Thr Gly
1               5                   10                  15

Val His Ser Asn Ile Met Met Thr Gln Ser Pro Ser Ser Leu Ala Val
                20                  25                  30

Ser Ala Gly Glu Lys Val Thr Met Ser Cys Lys Ser Ser His Ser Val
            35                  40                  45

Leu Tyr Ser Ser Asn Gln Lys Asn Tyr Leu Ala Trp Tyr Gln Gln Lys
        50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ile Asn Val His Thr Glu Asp Leu Ala Val Tyr Tyr
            100                 105                 110

Cys His Gln Tyr Leu Ser Ser Leu Thr Phe Gly Thr Gly Thr Lys Leu
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 9
<211> LENGTH: 475
<212> TYPE: PRT
<213> ORGANISM: Homo sapien

<400> SEQUENCE: 9

Met Gly Trp Ser Cys Ile Ile Leu Phe Leu Val Ala Thr Ala Thr Gly
1               5                   10                  15

Val His Ser Glu Ile Gln Leu Val Gln Ser Gly Pro Glu Leu Lys Lys
                20                  25                  30

Pro Gly Glu Thr Asn Lys Ile Ser Cys Lys Ala Ser Gly Tyr Thr Phe
            35                  40                  45

Thr Asn Tyr Gly Met Asn Trp Val Lys Gln Ala Pro Gly Lys Gly Leu
        50                  55                  60

Lys Trp Met Gly Trp Ile Asn Thr Tyr Thr Gly Glu Pro Thr Tyr Ala
```

```
            65                  70                  75                  80
Asp Asp Phe Thr Gly Arg Phe Ala Phe Ser Leu Glu Thr Ser Ala Ser
                85                  90                  95

Thr Ala Tyr Leu Gln Ile Ser Asn Leu Lys Asn Glu Asp Thr Ala Thr
            100                 105                 110

Tyr Phe Cys Ala Arg Asn Pro Ile Asn Tyr Tyr Gly Ile Asn Tyr Glu
        115                 120                 125

Gly Tyr Val Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 10
```

```
<211> LENGTH: 126
<212> TYPE: PRT
<213> ORGANISM: Artificial Sequence
<220> FEATURE:
<223> OTHER INFORMATION: VH 1

<400> SEQUENCE: 10

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Ile Asn Tyr Tyr Gly Ile Asn Tyr Glu Gly Tyr Val
            100                 105                 110

Met Asp Tyr Trp Gly Gln Gly Thr Leu Val Thr Val Ser Ser
        115                 120                 125

<210> SEQ ID NO 11
<211> LENGTH: 126
<212> TYPE: PRT
<213> ORGANISM: Artificial Sequence
<220> FEATURE:
<223> OTHER INFORMATION: VH 2

<400> SEQUENCE: 11

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Pro Ile Asn Tyr Tyr Gly Ile Asn Tyr Glu Gly Tyr Val
            100                 105                 110

Met Asp Tyr Trp Gly Gln Gly Thr Leu Val Thr Val Ser Ser
        115                 120                 125

<210> SEQ ID NO 12
<211> LENGTH: 126
<212> TYPE: PRT
<213> ORGANISM: Artificial Sequence
<220> FEATURE:
<223> OTHER INFORMATION: VH 3

<400> SEQUENCE: 12

Gln Val Gln Leu Val Gln Ser Gly Ser Glu Leu Lys Lys Pro Gly Ala
1               5                   10                  15
```

```
Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Thr Tyr Phe Cys
                85                  90                  95

Ala Arg Asn Pro Ile Asn Tyr Tyr Gly Ile Asn Tyr Glu Gly Tyr Val
            100                 105                 110

Met Asp Tyr Trp Gly Gln Gly Thr Leu Val Thr Val Ser Ser
        115                 120                 125

<210> SEQ ID NO 13
<211> LENGTH: 126
<212> TYPE: PRT
<213> ORGANISM: Artificial Sequence
<220> FEATURE:
<223> OTHER INFORMATION: VH 4

<400> SEQUENCE: 13

Gln Val Gln Leu Val Gln Ser Gly Ser Glu Leu Lys Lys Pro Gly Ala
 1               5                  10                  15

Ser Asn Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Thr Tyr Phe Cys
                85                  90                  95

Ala Arg Asn Pro Ile Asn Tyr Tyr Gly Ile Asn Tyr Glu Gly Tyr Val
            100                 105                 110

Met Asp Tyr Trp Gly Gln Gly Thr Leu Val Thr Val Ser Ser
        115                 120                 125

<210> SEQ ID NO 14
<211> LENGTH: 115
<212> TYPE: PRT
<213> ORGANISM: Artificial Sequence
<220> FEATURE:
<223> OTHER INFORMATION: VL 1

<400> SEQUENCE: 14

Asp Ile Val Met Thr Gln Ser Pro Asp Ser Leu Ala Val Ser Leu Gly
 1               5                  10                  15

Glu Arg Ala Thr Ile Asn Cys Lys Ser Ser His Ser Val Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80
```

```
Ile Ser Ser Leu Gln Ala Glu Asp Val Ala Val Tyr Tyr Cys His Gln
                85                  90                  95

Tyr Leu Ser Ser Leu Thr Phe Gly Gln Gly Thr Lys Leu Glu Ile Lys
            100                 105                 110

Arg Thr Val
        115

<210> SEQ ID NO 15
<211> LENGTH: 115
<212> TYPE: PRT
<213> ORGANISM: Artificial Sequence
<220> FEATURE:
<223> OTHER INFORMATION: VL 2

<400> SEQUENCE: 15

Asp Ile Val Met Thr Gln Ser Pro Asp Ser Leu Ala Val Ser Leu Gly
  1               5                  10                  15

Glu Arg Ala Thr Ile Asn Cys Lys Ser Ser His Ser Val Leu Tyr Ser
             20                  25                  30

Ser Asn Gln Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ile Asn Leu Gln Ala Glu Asp Val Ala Val Tyr Tyr Cys His Gln
                85                  90                  95

Tyr Leu Ser Ser Leu Thr Phe Gly Gln Gly Thr Lys Leu Glu Ile Lys
            100                 105                 110

Arg Thr Val
        115

<210> SEQ ID NO 16
<211> LENGTH: 115
<212> TYPE: PRT
<213> ORGANISM: Artificial Sequence
<220> FEATURE:
<223> OTHER INFORMATION: VL 3

<400> SEQUENCE: 16

Asp Ile Val Met Thr Gln Ser Pro Asp Ser Leu Ala Val Ser Leu Gly
  1               5                  10                  15

Glu Arg Ala Thr Ile Asn Cys Lys Ser Ser His Ser Val Leu Tyr Ser
             20                  25                  30

Ser Asn Gln Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu His Thr Glu Asp Val Ala Val Tyr Tyr Cys His Gln
                85                  90                  95

Tyr Leu Ser Ser Leu Thr Phe Gly Gln Gly Thr Lys Leu Glu Ile Lys
            100                 105                 110

Arg Thr Val
        115
```

```
<210> SEQ ID NO 17
<211> LENGTH: 115
<212> TYPE: PRT
<213> ORGANISM: Artificial Sequence
<220> FEATURE:
<223> OTHER INFORMATION: VL 4

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ser Ser His Ser Val Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ile Asn Leu His Thr Glu Asp Val Ala Val Tyr Tyr Cys His Gln
                85                  90                  95

Tyr Leu Ser Ser Leu Thr Phe Gly Gln Gly Thr Lys Leu Glu Ile Lys
            100                 105                 110

Arg Thr Val
        115

<210> SEQ ID NO 18
<211> LENGTH: 455
<212> TYPE: PRT
<213> ORGANISM: Artificial Sequence
<220> FEATURE:
<223> OTHER INFORMATION: Antibody A full length heavy chain.

<400> SEQUENCE: 18

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Ile Asn Tyr Tyr Gly Ile Asn Tyr Glu Gly Tyr Val
            100                 105                 110

Met Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190
```

```
Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
210                     215                 220

Glu Pro Lys Ser Cys Asp Lys Thr His Thr Cys Pro Pro Cys Pro Ala
225                 230                 235                 240

Pro Glu Leu Ala Gly Ala Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
290                 295                 300

Tyr Asn Ser Thr Tyr Arg Trp Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 19
<211> LENGTH: 219
<212> TYPE: PRT
<213> ORGANISM: Artificial Sequence
<220> FEATURE:
<223> OTHER INFORMATION: Antibody A full length light chain.

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ser Ser His Ser Val Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95
```

```
Tyr Leu Ser Ser Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```